US008530466B2

(12) United States Patent
Masuda et al.

(10) Patent No.: US 8,530,466 B2
(45) Date of Patent: Sep. 10, 2013

(54) USE OF 2,4-PYRIMIDINEDIAMINES FOR THE TREATMENT OF ATHEROSCLEROSIS

(75) Inventors: Esteban Masuda, Menlo Park, CA (US); Jochen Schmitz, Indianapolis, IN (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 151 days.

(21) Appl. No.: 12/867,928

(22) PCT Filed: Feb. 20, 2009

(86) PCT No.: PCT/US2009/034718
§ 371 (c)(1),
(2), (4) Date: Oct. 29, 2010

(87) PCT Pub. No.: WO2009/105675
PCT Pub. Date: Aug. 27, 2009

(65) Prior Publication Data
US 2011/0046126 A1    Feb. 24, 2011

Related U.S. Application Data

(60) Provisional application No. 61/030,903, filed on Feb. 22, 2008.

(51) Int. Cl.
*A61K 31/535* (2006.01)

(52) U.S. Cl.
USPC ........................................ 514/230.5; 514/824

(58) Field of Classification Search
USPC .......................................... 514/230.5, 234.5
See application file for complete search history.

(56) References Cited

U.S. PATENT DOCUMENTS 7,288,547 B2   10/2007  Lucking et al.

FOREIGN PATENT DOCUMENTS

| WO | 00/12485 A | 3/2000 |
|----|-----------|--------|
| WO | 00/39101 A | 7/2000 |
| WO | 03/002544 A | 1/2003 |
| WO | 03/062227 A | 7/2003 |
| WO | 2005/026158 A | 3/2005 |
| WO | WO 2006 078846 A1 * | 7/2006 |
| WO | 2006/108487 A | 10/2006 |
| WO | 2007/008541 A | 1/2007 |
| WO | 2007/053452 A | 5/2007 |
| WO | 2007/146977 A | 12/2007 |
| WO | 2008/005538 A | 1/2008 |
| WO | 2009/012421 A | 1/2009 |

OTHER PUBLICATIONS

Devaraj, S. et al., CRP promotes monocyte-endothelial cell adhesion via FC receptors in human aortic endothelial cells under static and shear flow conditions. AJP-Heart Circ. Physiol. 291, pp. H1170-H1176. Published Sep. 2006.*
Oliver, J.M., et al. Journal of Biological Chemistry. Vo. 269, pp. 29697-29703. Published 1994.*
Lee, H.M., et al. European Journal of Pharmacology. vol. 579 pp. 260-268. Published online Oct. 11, 2007.*
Hligendor, I., et al. Arterioscler Thromb Vasc Biol. vol. 31 pp. 1991-1999. Published 2011.*
Devaraj, S. et al., Am. J. Physiol Heart Circ Physiol. vol. 291 H1170-H1176. Published 2006.*
Ait-Oufella et al., J. Exp. Med., vol. 207, No. 8, 1579-1587 (2010).
Braselmann et al., J. Pharm. Exp. Ther., vol. 319, 998-1008 (2006).
Konishi et al., Circulation., vol. 105, 912-91 (2002).
Miura et al., Clinical and Experimental Allergy, vol. 31, 1732-1739 (2001).
Hilgendorf et al., Arterioscler Thromb Vase Biol., vol. 31, 1991-1999 (2011).

* cited by examiner

*Primary Examiner* — Paul Zarek
*Assistant Examiner* — George W Kosturko
(74) *Attorney, Agent, or Firm* — Travis Young; McDonnell Boehnen Hulbert & Berghoff LLP

(57) ABSTRACT

Novel methods and compositions for the prevention and treatment of all forms of atherosclerosis with 2,4-pyrimidinediamine compounds are described. Also disclosed is the coating of prosthetic devices, such as stents, with the compounds of the invention for the prevention and/or treatment of restenosis.

1 Claim, 2 Drawing Sheets

USE OF 2,4-PYRIMIDINEDIAMINES FOR THE TREATMENT OF ATHEROSCLEROSIS

I. INTRODUCTION

A. Field of the Invention

Figure 1:
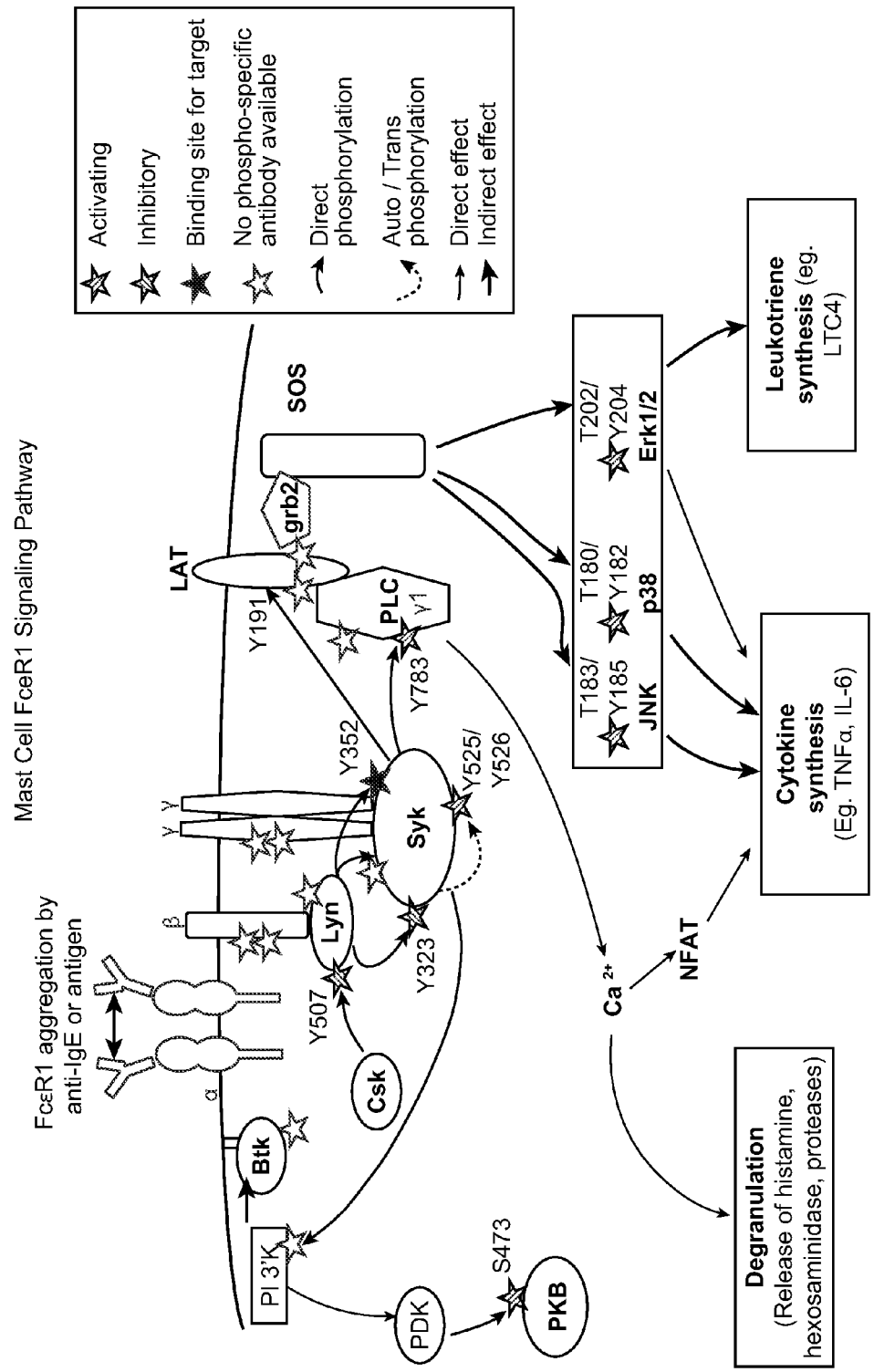

The present invention relates generally to the field of pharmaceutical treatment of atherosclerosis and its associated cardiovascular risk.

B. Background of the Invention

Cardiovascular disease, principally heart disease and stroke, kills approximately one million Americans each year, making it the number one killer in the United States. Elevated cholesterol levels in the blood have long been recognized as a risk factor and precursor for a wide range of health problems. Cardiovascular disease includes conditions that lead to narrowing or blockage of the heart, arteries, and veins. Atherosclerosis, often described as a hardening of the arteries, occurs when the normal lining of the arteries deteriorates, the walls of arteries thicken, and deposits of fat and plaque build up within the arteries, causing narrowing (or even blockage). Hypertension, or high blood pressure, results from narrowing of vessels due to similar deposits, which reduces the blood supply to all areas of the body, and causes the heart to work harder to pump the same amount of blood. Inadequate oxygen flow to the brain causes stroke.

Environmental pollution, daily stress, and lifestyle behaviors can all contribute to cardiovascular disease, as do a number of health-related behaviors, including tobacco use, lack of physical activity, and poor nutrition. Traditional treatment approaches include medication and surgery, and many scientific studies show a positive effect from changes in diet and lifestyle. Thus, optimal treatment regimens can be complex.

Cardiovascular disease is the leading killer in the developed world, with U.S., deaths from heart disease and stroke accounting for 35% of annual mortality. Cholesterol-lowering drugs are one of the most successful therapies in the world, generating over $27B in 2005 alone. While it is clear that lowering "bad" cholesterol (LDL, low-density lipoproteins) can help prevent a host of serious cardiovascular events and raising "good" cholesterol levels (HDL, high-density lipoproteins) correlates with improved cardiac health, cholesterol levels alone are not the only important factor determining cardiovascular risk. Thus, it is important to understand the links between high cholesterol, increased build-up of fatty deposits (plaque) in the arteries, and heart disease, so that treatments can be optimized to specific patients.

A connection between mast cells and the pathogenesis of atherosclerosis was first suggested in 1953 (Constantinides, *Science* 117: 505-6 (1953); Cairns et al., *Science* 120: 31-2 (1954)). Subsequent research has supported this proposition (see Kovanen, *Immunol. rev.* 217:105-122 (2007), incorporated herein by reference). For example, the number of activated mast cells in atherosclerotic plaques is especially high in the shoulder regions prone to plaque rupture as compared to normal intima. Further, the number of plaque erosions and the proportion of mast cells associated with erosions increases markedly as the disease becomes more severe. A significant mechanism leading to plaque rupture is the increased degradation of extracellular and pericellular matrix components in the fibrous cap. Activated mast cells secrete proteases, such as tryptase and chymase, that inactivate HDL and enhance degradation of the extracellular matrix via activation of matrix metalloproteinases (MMPs). The heparin proteoglycan component of the exocytosed granules bind apolipoprotein (apo)B-100 of LDL particles and lead to uptake of the LDL by macrophages and foam cells and ultimately to deposition of fatty streaks in the vascular plaque. Histamine released by activated mast cells also triggers coronary spasm, which can lead to plaque rupture and erosion. Thus pharmaceutical intervention aimed at inhibiting mast cell activation and subsequent degranulation is expected to inhibit both the development and progression of atherosclerosis.

A key step in mast cell activation is the cross-linking of Fc receptors, such as the high affinity receptor for IgE (FcεRI) and/or the high affinity receptor for IgG (FcγRI). Such cross-linking activates a signaling cascade in mast and other immune cells that results in the release of chemical mediators responsible for numerous adverse events. For example, such cross-linking leads to the release of preformed mediators, such as histamine and proteases, from storage sites in granules via degranulation. It also leads to the synthesis and release of other mediators, including growth factors, various cytokines and platelet-activating factors (PAPs), that play important roles in the development and progression of atherosclerosis. The signaling cascade(s) activated by cross-linking Fc receptors such as FcεRI and/or FcγRI comprises an array of cellular proteins (see FIG. 1). Among the most important intracellular signal propagators are the tyrosine kinases. And, an important tyrosine kinase involved in the signal transduction pathways associated with crosslinking the FcεRI and/or FcγRI receptors, as well as other signal transduction cascades, is Syk kinase (see Valent et al., 2002, Inti. J. Hematol. 75(4):257-362 for review).

Second, platelets play a pivotal role in the late stage of atherosclerosis, during plaque rupture and thrombus formation. In particular, platelet P-selectin has been demonstrated to play a critical role in the development of atherosclerosis (Huo et al., *Nat Med.* 9:61-67 (2003); Burger et al., *Blood* 101: 2661-2666 (2003)). CD62P participates in the early steps of leukocyte recruitment and mediates interactions of platelets and leukocytes with the damaged vessel wall through multiple mechanisms. P-selectin (CD62P) is constitutively expressed and stored in the α-granules of platelets and translocated rapidly to the cell surface in response to several inflammatory stimuli. Activation and degranulation by platelets is also mediated by the Syk pathway.

As the mediators released as a result of FcεRI and FcγRI receptor cross-linking in mast cells and platelets are responsible for, or play important roles in, the development and progression of atherosclerosis, the availability of compounds capable of inhibiting the signaling cascade(s) responsible for their release would be highly desirable.

II. SUMMARY OF THE INVENTION

Novel methods and compositions for the prevention and treatment of all forms of atherosclerosis with 2,4 pyrimidinediamine compounds are described. Also disclosed is the coating of prosthetic devices, such as stents, with the compounds of the invention for the prevention and/or treatment of restenosis.

One aspect of the invention provides methods of treating atherosclerosis or regressing or decreasing formation of arterial atherosclerotic lesions, said method comprising administering to a mammal having atherosclerosis an effective amount of a Syk kinase inhibitor.

Another aspect of the invention provides methods of treating atherosclerosis or regressing or decreasing formation of arterial atherosclerotic lesions, said method comprising administering to a mammal having atherosclerosis an effective amount of a compound of structural formula I:

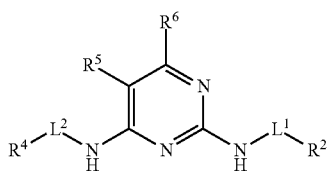

I wherein:
- $L^1$ and $L^2$ are each, independently of one another, selected from the group consisting of a direct bond and a linker;
- $R^2$ is selected from the group consisting of $C_{1-6}$ alkyl optionally substituted with one or more of the same or different $R^8$ groups, $C_{3-8}$ cycloalkyl optionally substituted with one or more of the same or different $R^8$ groups, cyclohexyl optionally substituted with one or more of the same or different $R^8$ groups, 3-8 membered cycloheteroalkyl optionally substituted with one or more of the same or different $R^8$ groups, $C_{5-15}$ aryl optionally substituted with one or more of the same or different $R^8$ groups, phenyl optionally substituted with one or more of the same or different $R^8$ groups and 5-15 membered heteroaryl optionally substituted with one or more of the same or different $R^8$ groups;
- $R^4$ is selected from the group consisting of hydrogen, $C_{1-6}$ alkyl optionally substituted with one or more of the same or different $R^8$ groups, $C_{3-8}$ cycloalkyl optionally substituted with one or more of the same or different $R^8$ groups, 3-8 membered cycloheteroalkyl optionally substituted with one or more of the same or different $R^8$ groups, $C_{5-15}$ aryl optionally substituted with one or more of the same or different $R^8$ groups, and 5-15 membered heteroaryl optionally substituted with one or more of the same or different $R^8$ groups;
- $R^5$ is selected from the group consisting of $R^6$, $C_{1-6}$ alkyl optionally substituted with one or more of the same or different $R^8$ groups; each $R^6$ is independently selected from the group consisting of hydrogen, an electronegative group, —$OR^d$, —$SR^d$, $C_{1-3}$ haloalkyloxy, $C_{1-3}$ perhaloalkyloxy, —$NR^cR^c$, halogen, $C_{1-3}$ haloalkyl, $C_{1-3}$ perhaloalkyl, —$CF_3$, —$CH_2CF_3$, —$CF_2CF_3$, —CN, —NC, —OCN, —SCN, —NO, —$NO_2$, —$N_3$, —S(O)$R^d$, —S(O)$_2R^d$, —S(O)$_2OR^d$, —S(O)$NR^cR^c$, —OS(O)$R^d$, —OS(O)$_2R^d$, —OS(O)$_2OR^d$, —OS(O)$NR^cR^c$, —OS(O)$_2NR^cR^c$, —C(O)$R^d$, —C(O)$OR^d$, —C(O)$NR^cR^c$, —C(NH)$NR^cR^c$, —OC(O)$R^d$, —SC(O)$R^d$, —OC(O)$OR^d$, —SC(O)$OR^d$, —OC(O)$NR^cR^c$, —SC(O)$NR^cR^c$, —OC(NH)$NR^cR^c$, —SC(NH)$NR^cR^c$, —[NHC(O)]$_nR^d$—, —[NHC(O)]$_nOR^d$, —[NHC(O)]$_nNR^cR^c$ and —[NHC(NH)]$_nNR^cR^c$, $C_{5-10}$ aryl optionally substituted with one or more of the same or different $R^8$ groups, $C_{6-16}$ arylalkyl optionally substituted with one or more of the same or different $R^8$ groups, 5-10 membered heteroaryl optionally substituted with one or more of the same or different $R^8$ groups and 6-16 membered heteroarylalkyl optionally substituted with one or more of the same or different $R^8$ groups;
- $R^8$ is selected from the group consisting of $R^a$, $R^b$, $R^e$ substituted with one or more of the same or different $R^a$ or $R^b$, —$OR^a$ substituted with one or more of the same or different $R^a$ or $R^b$, —B($OR^a$)$_2$, —B($NR^cR^c$)$_2$, —(CH$_2$)$_m$—$R^b$, —(CHR$^a$)$_m$—$R^b$, —O—(CH$_2$)$_m$—$R^b$, —S(CH$_2$)$_m$—$R^b$, —O—CHR$^a$R$^b$, —O—CR$^a$(R$^a$)$_2$, —O—(CHR$^a$)$_m$—$R^b$, —O—(CH$_2$)$_m$—CH[(CH$_2$)$_mR^b$] $R^b$, —S—(CHR$^a$)$_m$—$R^b$; —C(O)NH—(CH$_2$)$_m$—$R^b$, —C(O)NH—(CHR$^a$)$_m$—$R^b$, —O(CH$_2$)$_m$—C(O)NH—(CH$_2$)$_m$—$R^b$, —S—(CH$_2$)$_m$—$R^b$, —C(O)NH—(CH$_2$)$_mR^b$, —O—(CHR$^a$)$_m$—C(O)NH—(CHR$^a$)$_m$-$R^b$, —S—(CHR$^a$)$_m$—C(O)NH—(CHR$^a$)$_m$—$R^b$, —NH—(CH$_2$)$_m$—$R^b$, —NH—(CHR$^a$)$_m$—$R^b$, —NH[(CH$_2$)$_mR^b$], —N[(CH$_2$)$_mR^b$]$_2$, —NH—C(O)—NH—(CH$_2$)$_m$—$R^b$, —NH—C(O)—(CH$_2$)$_m$—CHR$^b$R$^b$ and —NH—(CH$_2$)$_m$—C(O)—NH—(CH$_2$)$_m$—$R^b$;
- each $R^a$ is independently selected from the group consisting of hydrogen, $C_{1-6}$ alkyl, $C_{3-8}$ cycloalkyl, $C_{4-11}$ cycloalkylalkyl, $C_{5-10}$ aryl, $C_{6-16}$ arylalkyl, 2-6 membered heteroalkyl, 3-8 membered cycloheteroalkyl, 4-11 membered cycloheteroalkylalkyl, 5-10 membered heteroaryl and 6-16 membered heteroarylalkyl;
- each $R^b$ is independently selected from the group consisting of =O, —$OR^d$, (C1-C3) haloalkyloxy, —$OCF_3$, =S, —$SR^d$, =$NR^d$, =$NOR^d$, —$NR^cR^c$, halogen, —$CF_3$, —CN, —NC, —OCN, —SCN, —NO, —$NO_2$, =$N_2$, —$N_3$, —S(O)$R^d$, —S(O)$_2R^d$, —S(O)$_2OR^d$, —S(O)$NR^cR^c$, —S(O)$_2NR^cR^c$, —OS(O)$R^d$, —OS(O)$_2R^d$, —OS(O)$_2OR^d$, —OS(O)$_2NR^cR^c$, —C(O)$R^d$, —C(O)$OR^d$, —C(O)$NR^cR^c$, —C(NH)$NR^cR^c$, —C($NR^a$)$NR^cR^c$, —C(NOH)$R^a$, —C(NOH)$NR^cR^c$, —OC(O)$R^d$, —OC(O)$OR^d$, —OC(O)$NR^cR^c$, —OC(NH)$NR^cR^c$, —OC($NR^a$)$NR^cR^c$, —[NHC(O)]$_nR^d$, —[$NR^a$C(O)]$_nR^d$, —[NHC(O)]$_nOR^d$, —[$NR^a$C(O)]$_nOR^d$, —[NHC(O)]$_nNR^cR^c$, —[$NR^a$C(O)]$_n$ $NR^cR^c$, —[NHC(NH)]$_nNR^cR^c$ and —[$NR^a$C($NR^a$)]$_nNR^cR^c$;
- each $R^c$ is independently a protecting group or $R^a$, or, alternatively, each $R^c$ is taken together with the nitrogen atom to which it is bonded to form a 5 to 8-membered cycloheteroalkyl or heteroaryl which may optionally include one or more of the same or different additional heteroatoms and which may optionally be substituted with one or more of the same or different $R^a$ or $R^b$ groups;
- each $R^d$ is independently a protecting group or $R^a$;
- each $R^e$ is independently selected from the group consisting of $C_{1-6}$ alkyl, $C_{3-8}$ cycloalkyl, $C_{4-11}$ cycloalkylalkyl, $C_{5-10}$ aryl, $C_{6-16}$ arylalkyl, 2-6 membered heteroalkyl, 3-8 membered cycloheteroalkyl, 4-11 membered cycloheteroalkylalkyl, 5-10 membered heteroaryl and 6-16 membered heteroarylalkyl;
- each m is independently an integer from 1 to 3; and
- each n is independently an integer from 0 to 3.

Yet another aspect of the invention provides methods of treating atherosclerosis or regressing or decreasing formation of arterial atherosclerotic lesions, said method comprising administering to a mammal having atherosclerosis an effective amount of a compound of formula II:

II wherein:
- Y is selected from $CH_2$, $NR^{24}$, O, S, S(O) and S(O)$_2$;
- $Z^1$ and $Z^2$ each, independently of one another, are selected from CH and N;
- $R^2$ is selected from (C1-C6) alkyl optionally substituted with one or more of the same or different $R^8$ groups, (C3-C8) cycloalkyl optionally substituted with one or more of the same or different $R^8$ groups, 3-8 membered cycloheteroalkyl optionally substituted with one or more of the same or different $R^8$ groups, (C6-C14) aryl optionally substituted with one or more of the same or different $R^8$ groups, and 5-15 membered heteroaryl optionally substituted with one or more of the same or different $R^8$ groups;

$R^5$ is selected from halo, cyano, nitro, and trihalomethyl;

$R^8$ is selected from $R^a$, $R^b$, $R^a$ substituted with one or more of the same or different $R^a$ or $R^b$, —$OR^a$ substituted with one or more of the same or different $R^a$ or $R^b$, —$B(OR^a)_2$, —$B(NR^cR^c)_2$, —$(CH_2)_m$—$R^b$, —$(CHR^a)_m$—$R^b$, —O—$(CH_2)_m$—$R^b$, —S—$(CH2)_m$—$R^b$, —O—$CHR^aR^b$, —O—$CR^a(R^b)_2$, —O—$(CHR^a)_m$—$R^b$, —O—$(CH_2)_m$—CH[$(CH_2)_mR^b$]$R^b$, —S—$(CHR^a)_m$—$R^b$, —C(O)NH—$(CH_2)_m$—$R^b$, —C(O)NH—$(CHR^a)_m$—Rb, —O—$(CH_2)_m$—C(O)NH—$(CH_2)_m$—$R^b$, —S—$(CH_2)_m$—C(O)NH—$(CH2)_m$—$R^b$, —O—$(CHR^a)_m$—C(O)NH—$(CHR^a)_m$—$R^b$, —S—$(CHR^a)_m$—C(O)NH—$(CHR^a)_m$—$R^b$, —NH—$(CH_2)_m$—$R^b$, —NH—$(CHR^a)_m$—$R^b$, —NH[$(CH_2)_mR^b$], —N[$(CH_2)_mR^b$]$_2$, —NH—C(O)—NH—$(CH_2)_m$—$R^b$, —NH—C(O)—$(CH_2)_m$—$CHR^bR^b$ and —NH—$(CH_2)_m$—C(O)—NH—$(CH_2)_m$—$R^b$;

$R^{17}$ is selected from hydrogen, halogen, and lower alkyl or, alternatively, $R^{17}$ may be taken together with $R^{18}$ to form an oxo (=O) group or, together with the carbon atom to which they are attached, a spirocycle containing from 3 to 7 carbon atoms;

$R^{18}$ is selected from hydrogen, halogen, and lower alkyl or, alternatively, $R^{18}$ may be taken together with $R^{17}$ to form an oxo (=O) group or, together with the carbon atom to which they are attached, a spirocycle containing from 3 to 7 carbon atoms;

$R^{19}$ is selected from hydrogen and lower alkyl or, alternatively, $R^{19}$ may be taken together with $R^{20}$ to form an oxo (=O) group or, together with the carbon atom to which they are attached, a spirocycle containing from 3 to 7 carbon atoms;

$R^{20}$ is selected from hydrogen and lower alkyl or, alternatively, $R^{20}$ may be taken together with $R^{19}$ to form an oxo (=O) group or, together with the carbon atom to which they are attached, a spirocycle containing from 3 to 7 carbon atoms;

each $R^a$ is, independently of the others, selected from hydrogen, lower alkyl, lower cycloalkyl, (C4-C11) cycloalkylalkyl, (C6-C10) aryl, (C7-C16) arylalkyl, 2-6 membered heteroalkyl, 3-8 membered cycloheteroalkyl, 4-11 membered cycloheteroalkylalkyl, 5-10 membered heteroaryl and 6-16 membered heteroarylalkyl;

each $R^b$ is independently selected from =O, —$OR^a$, (C1-C3) haloalkyloxy, =S, —$SR^a$, =$NR^a$, =$NOR^a$, —$NR^cR^c$, halogen, —$CF_3$, —CN, —NC, —OCN, —SCN, —NO, —$NO_2$, =$N_2$, —$N_3$, —$S(O)R^a$, —$S(O)_2R^a$, —$S(O)_2OR^a$, —$S(O)NR^cR^c$, —$S(O)_2NR^cR^c$, —$OS(O)R^a$, —$OS(O)_2R^a$, —$OS(O)_2OR^a$, —$OS(O)_2NR^cR^c$, —$C(O)R^a$, —$C(O)OR^a$, —$C(O)NR^cR^c$, —$C(NH)NR^cR^c$, —$C(NR^a)NR^cRc$, —$C(NOH)R^a$, —$C(NOH)NR^cR^c$, —$OC(O)R^a$, —$OC(O)OR^a$, —$OC(O)NR^cR^c$, —$OC(NH)NR^cR^c$, —$OC(NR^a)NR^cR^c$, —[NHC(O)]$_n$$R^a$, —[$NR^aC(O)$]$_n$$R^a$, —[NHC(O)]$_n$$OR^a$, —[$NR^aC(O)$]$_n$$OR^a$, —[NHC(O)]$_n$$NR^cR^c$, —[$NR^aC(O)$]$_n$$NR^cR^c$, —[NHC(NH)]$_n$$NR^cR^c$ and —[$NR^aC(NR^a)$]$_n$$NR^cR^c$;

each $R^c$ is, independently of the others, selected from a protecting group and $R^a$, or, alternatively, the two $R^c$ bonded to the same nitrogen atom are taken together with that nitrogen atom to form a 5 to 8-membered cycloheteroalkyl or heteroaryl which may optionally include one or more of the same or different additional heteroatoms and which may optionally be substituted with one or more of the same or different $R^a$ groups;

$R^{21}$, $R^{22}$ and $R^{23}$ are each, independently of one another, selected from hydrogen and a progroup $R^P$;

$R^P$ has the formula —$(CR^dR^d)_y$-A-$R^3$, where y is an integer ranging from 1 to 3; A is O or S; each $R^d$ is, independently of the others, selected from hydrogen, optionally substituted lower alkyl, optionally substituted (C6-C14) aryl and optionally substituted (C7-C20) arylalkyl; where the optional substituents are, independently of one another, selected from hydroxyl, lower alkoxy, (C6-C14) aryloxy, lower alkoxyalkyl and halogen, or, alternatively, two $R^d$ bonded to the same carbon atom, taken together with the carbon atom to which they are bonded, form a cycloalkyl group containing from 3 to 8 carbon atoms;

$R^3$ comprises, together with the heteroatom, A, to which it is bonded, an alcohol, an ether, a thioether, a silyl ether, a silyl thioether, an ester, a thioester, an amide, a carbonate, a thiocarbonate, a carbamate, a thiocarbamate, a urea, a phosphate, a phosphate salt or a phosphate ester;

each m is, independently of the others, an integer from 1 to 3; and each n is, independently of the others, an integer from 0 to 3, with the proviso that at least one of $R^{21}$, $R^{22}$, and $R^{23}$ is $R^P$.

III. BRIEF DESCRIPTION OF THE DRAWINGS

The skilled artisan will understand that the drawings, described below, are for illustration purposes only. The drawings are not intended to limit the scope of the present teaching in any way.

FIG. 1 provides a cartoon illustrating the FcεR1 signal transduction cascade leading to degranulation of mast cells.

Figure 2:
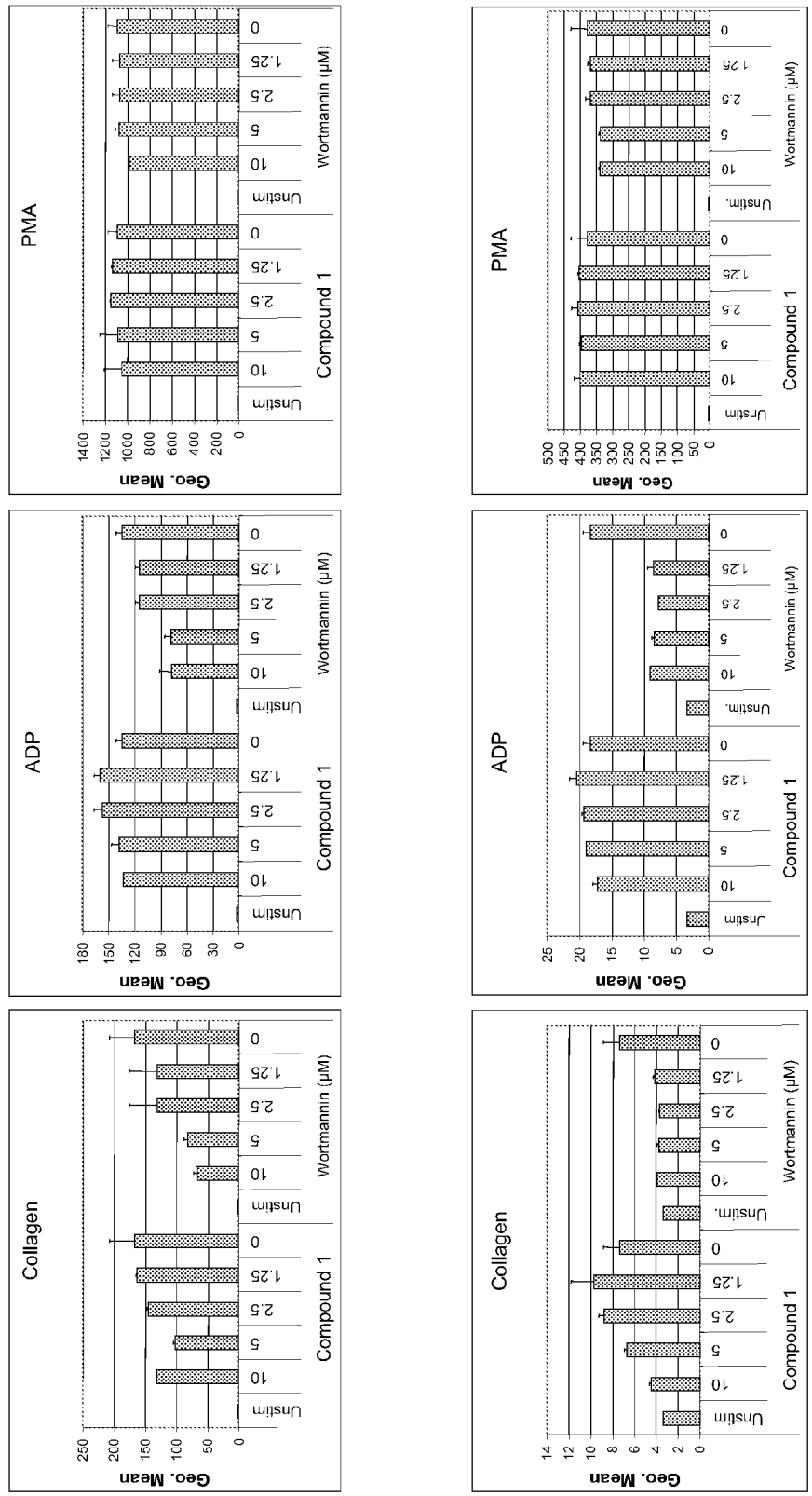

FIG. 2 provides the results of collagen, ADP and PMA-induced surface expression of CD62P by platelets treated with a 2,4 pyrimidinediamine of the invention or wortmannin.

IV. DETAILED DESCRIPTION

A. Overview

The invention encompasses novel methods and compositions for the prevention and treatment of all forms of atherosclerosis with 2,4 pyrimidinediamine compounds are described. Also disclosed is the coating of prosthetic devices, such as stents, with the compounds of the invention for the prevention and/or treatment of restenosis.

B. Definitions

As used herein, the following definitions shall apply unless otherwise indicated.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$$CHCH_2$—), sec-butyl (($CH_3$)($CH_3CH_2$)CH—), t-butyl (($CH_3$)$_3$C—), n-pentyl ($CH_3CH_2CH_2CH_2CH_2$—), and neopentyl (($CH_3$)$_3$$CCH_2$—).

"Substituted alkyl" refers to an alkyl group having from 1 to 5 hydrogens replaced with substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, sulfonylamino, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, sulfonyl, sulfonyloxy, thioacyl, thiol, alkylthio, and substituted alkylthio, wherein said substituents are defined herein. In some embodiments, the alkyl has 1 to 3 of the aforementioned groups. In other embodiments, the alkyl has 1 to 2 of the aforementioned groups.

"Alkylene" refers to divalent saturated aliphatic hydrocarbyl groups preferably having from 1 to 6 and more preferably 1 to 3 carbon atoms that are either straight-chained or branched. This term is exemplified by groups such as methylene (—$CH_2$—), ethylene (—$CH_2CH_2$—), n-propylene (—$CH_2CH_2CH_2$—), iso-propylene (—$CH_2CH(CH_3)$—) or (—$CH(CH_3)CH_2$—), and the like.

"Substituted alkylene" refers to an alkylene group having from 1 to 3 hydrogens replaced with substituents selected from the group consisting of alkyl, substituted alkyl, alkoxy, substituted alkoxy, acyl, acylamino, acyloxy, amino, substituted amino, aminocarbonyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, substituted heterocyclic, and oxo wherein said substituents are defined herein. In some embodiments, the alkylene has 1 to 2 of the aforementioned groups. It is to be noted that when the alkylene is substituted by an oxo group, 2 hydrogens attached to the same carbon of the alkylene group are replaced by "=O".

"Alkoxy" refers to the groups —O-alkyl, —O-alkenyl, and —O-alkynyl, wherein alkyl, alkenyl and alkynyl are as defined herein.

"Substituted alkoxy" refers to the groups —O-(substituted alkyl), —O-(substituted alkenyl), and —O-(substituted alkynyl), wherein substituted alkyl, substituted alkenyl, and substituted alkynyl are as defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)-cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Acyl includes the "acetyl" group $CH_3C(O)$—.

"Acylamino" refers to the groups —$NR^{20}$C(O)alkyl, —$NR^{20}$C(O)substituted alkyl, —$NR^{20}$C(O)cycloalkyl, —$NR^{20}$C(O)substituted cycloalkyl, —$NR^{20}$C(O)cycloalkenyl, —$NR^{20}$C(O)substituted cycloalkenyl, —$NR^{20}$C(O)alkenyl, —$NR^{20}$C(O)substituted alkenyl, —$NR^{20}$C(O)alkynyl, —$NR^{20}$C(O)substituted alkynyl, —$NR^{20}$C(O)aryl, —$NR^{20}$C(O)substituted aryl, —$NR^{20}$C(O)heteroaryl, —$NR^{20}$C(O)substituted heteroaryl, —$NR^{20}$C(O)heterocyclic, and —$NR^{20}$C(O)substituted heterocyclic, wherein $R^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group —$NH_2$.

"Substituted amino" refers to the group —$NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, where one of $R^{21}$ and $R^{22}$ is sulfonyl, and wherein $R^{21}$ and $R^{22}$ are optionally joined together with the nitrogen bound thereto to form a heterocyclic or substituted heterocyclic group, provided that $R^{21}$ and $R^{22}$ are not both hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, sulfonyl, substituted heteroaryl, heterocyclic, and substituted heterocyclic are as defined herein. When $R^{21}$ is hydrogen and $R^{22}$ is alkyl, the substituted amino group is sometimes referred to herein as "alkylamino." When $R^{21}$ and $R^{22}$ are alkyl, the substituted amino group is sometimes referred to herein as "dialkylamino." When referring to a monosubstituted amino, it is meant that either $R^{21}$ or $R^{22}$ is hydrogen, but not both. When referring to a disubstituted amino, it is meant that neither $R^{21}$ nor $R^{22}$ is hydrogen.

"Aminocarbonyl" refers to the group —C(O)$NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonyl" refers to the group —C(S)$NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —$NR^{20}C(O)NR^{21}R^{22}$ wherein $R^{20}$ is hydrogen or alkyl and $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonylamino" refers to the group —$NR^{20}C(S)NR^{21}R^{22}$, wherein $R^{20}$ is hydrogen or alkyl and $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonyloxy" refers to the group —O—$C(O)NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyl" refers to the group —$SO_2NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where $R^{21}$ and $R^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyloxy" refers to the group —O—$SO_2NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic; $R^{21}$ and $R^{22}$ are optionally joined together with the nitrogen bound thereto to form a heterocyclic or substituted heterocyclic group; and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonylamino" refers to the group —$NR^{20}$—$SO_2NR^{21}R^{22}$, wherein $R^{20}$ is hydrogen or alkyl and $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —$NR^{21}SO_2R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amidino" refers to the group —$C(=NR^{30})NR^{31}R^{32}$, wherein $R^{31}$ and $R^{32}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{31}$ and $R^{32}$ are optionally joined together with the nitrogen bound thereto to form a heterocyclic or substituted heterocyclic group. $R^{30}$ is selected from the group consisting of hydrogen, alkyl, substituted alkyl, alkenyl, substituted alkenyl, alkynyl, substituted alkynyl, cycloalkynyl, substituted cycloalkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, nitro, nitroso, hydroxy, alkoxy, cyano, acyl, —$SO_2$-alkyl and —$SO_2$-substituted alkyl, wherein alkyl, substituted alkyl, alkenyl, substituted alkenyl, alkynyl, substituted alkynyl, cycloalkynyl, substituted cycloalkynyl, cycloalkyl, substituted cycloalkyl, cycloalkenyl, substituted cycloalkenyl, aryl, substituted aryl, heteroaryl, substituted heteroaryl, heterocyclic, substituted heterocyclic, nitro, nitroso, hydroxy, alkoxy, and cyano are as defined herein.

"Aryl" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic provided that the point of attachment is through an atom of the aromatic aryl group. As used herein multiple rings refers to fused, bridged or spiro ring systems consisting of 2, 3 or 4 rings. For example, 1,2,3,4-tetrahydronaphthalen-5-yl, 9H-fluoren-2-yl, and the like. Preferred aryl groups include phenyl and naphthyl.

"Substituted aryl" refers to aryl groups having 1 to 5 hydrogens replaced with substituents independently selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, sulfonyl, sulfonyloxy, thioacyl, thiol, alkylthio, and substituted alkylthio, wherein said substituents are as defined herein. In some embodiments, the aryl has 1 to 3 of the aforementioned groups. In other embodiments, the aryl has 1 to 2 of the aforementioned groups. In some embodiments, substituted aryl includes compounds containing oxo substituent in the non-aromatic ring fused to the aryl group. For example, 1-oxo-indan-4-yl, wherein the point of attachment is through the phenyl ring.

"Aryloxy" refers to the group —O-aryl, wherein aryl is as defined herein, including, by way of example, phenoxy, naphthoxy, and the like.

"Substituted aryloxy" refers to the group —O-(substituted aryl), wherein substituted aryl is as defined herein.

"Arylthio" refers to the group —S-aryl, wherein aryl is as defined herein. In other embodiments, sulfur may be oxidized to —S(O)— or —SO$_2$— moieties. The sulfoxide may exist as one or more stereoisomers.

"Substituted arylthio" refers to the group —S-(substituted aryl), wherein substituted aryl is as defined herein. In other embodiments, sulfur may be oxidized to —S(O)— or —SO$_2$— moieties. The sulfoxide may exist as one or more stereoisomers.

"Alkenyl" refers to straight chain or branched hydrocarbyl groups having from 2 to 6 carbon atoms and preferably 2 to 4 carbon atoms and having at least 1 and preferably from 1 to 2 sites of vinyl (>C=C<) unsaturation. Such groups are exemplified by vinyl, allyl, and but-3-en-1-yl. Included within this term are the cis and trans isomers or mixtures of these isomers.

"Substituted alkenyl" refers to alkenyl groups having from 1 to 3 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, sulfonyl, sulfonyloxy, thioacyl, thiol, alkylthio, and substituted alkylthio, wherein said substituents are as defined herein and with the proviso that any hydroxy substitution is not attached to a vinyl (unsaturated) carbon atom. In some embodiments, the alkenyl has 1 to 2 of the aforementioned groups.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic —C≡C— unsaturation. Examples of such alkynyl groups include acetylenyl (—C≡CH), and propargyl (—CH$_2$C≡CH).

"Substituted alkynyl" refers to alkynyl groups having from 1 to 3 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, sulfonyl, sulfonyloxy, thioacyl, thiol, alkylthio, and substituted alkylthio, wherein said substituents are as defined herein and with the proviso that any hydroxy or thiol substitution is not attached to an acetylenic carbon atom. In some embodiments, the alkynyl has 1 to 2 of the aforementioned groups.

"Alkynyloxy" refers to the group —O-alkynyl, wherein alkynyl is as defined herein. Alkynyloxy includes, by way of example, ethynyloxy, propynyloxy, and the like.

"Carboxyl" or "carboxy" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)amino" refers to the groups —NR—C(O)O-alkyl, —NR—C(O)O-substituted alkyl, —NR—C(O)O-alkenyl, —NR—C(O)O-substituted alkenyl, —NR—C(O)O-alkynyl, —NR—C(O)O-substituted alkynyl, —NR—C(O)O-aryl, —NR—C(O)O-substituted aryl, —NR—C(O)O-cycloalkyl, —NR—C(O)O-substituted cycloalkyl, —NR—C(O)O-cycloalkenyl, —NR—C(O)O-substituted cycloalkenyl, —NR—C(O)O-heteroaryl, —NR—C(O)O-substituted heteroaryl, —NR—C(O)O-heterocyclic, and —NR—C(O)O-substituted heterocyclic, wherein R is alkyl or hydrogen and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" refers to the groups —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 13 carbon atoms having single or multiple cyclic rings including fused, bridged, and spiro ring systems. Examples of cycloalkyl groups include adamantyl, cyclopropyl, cyclobutyl, cyclopentyl, cyclooctyl, and the like. One or more rings fused to the cycloalkyl group can be aromatic, provided that the point of attachment is through the non-aromatic ring, e.g. 9H-fluoren-9-yl, 1,2,3,4-tetrahydronaphthalen-2-yl, and the like.

"Cycloalkenyl" refers to non-aromatic cyclic alkyl groups of from 3 to 10 carbon atoms having single or multiple rings and having at least one double bond and preferably from 1 to 2 double bonds.

"Cycloalkynyl" refers to non-aromatic cycloalkyl groups of from 7 to 12 carbon atoms having single or multiple rings and having at least one triple bond.

"Cycloalkylene" refers to divalent cycloalkyl groups, wherein cycloalkyl is as defined herein.

"Substituted cycloalkylene" refers to cycloalkylene group having from 1 to 3 hydrogens replaced with substituents selected from the group consisting of alkyl, substituted alkyl, alkoxy, substituted alkoxy, acyl, acylamino, acyloxy, amino, substituted amino, aminocarbonyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, substituted heterocyclic, and oxo wherein said substituents are as defined herein. In some embodiments, the alkylene has 1 to 2 of the aforementioned groups. It is to be noted that when the cycloalkylene is substituted by an oxo group, 2 hydrogens attached to the same carbon of the cycloalkylene group are replaced by "=O".

"Substituted cycloalkyl," "substituted cycloalkenyl," and "substituted cycloalkynyl" refer to a cycloalkyl, cycloalkenyl, or cycloalkynyl group having from 1 to 5 substituents selected from the group consisting of oxo, thioxo, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, sulfonyl, sulfonyloxy, thioacyl, thiol, alkylthio, and substituted alkylthio, wherein said substituents are as defined herein, provides that any hydroxy or thiol substitution is not attached to an unsaturated carbon atom. In some embodiments, the cycloalkyl or cycloalkenyl has 1 to 3 of the aforementioned groups.

"Cycloalkoxy" refers to —O-cycloalkyl.

"Substituted cycloalkoxy" refers to —O-(substituted cycloalkyl).

"Cycloalkylthio" refers to —S-cycloalkyl. In other embodiments, sulfur may be oxidized to —S(O)— or —$SO_2$— moieties. The sulfoxide may exist as one or more stereoisomers.

"Substituted cycloalkylthio" refers to —S-(substituted cycloalkyl). In other embodiments, sulfur may be oxidized to —S(O)—, or —$SO_2$— moieties. The sulfoxide may exist as one or more stereoisomers.

"Cycloalkenyloxy" refers to —O-cycloalkenyl.

"Substituted cycloalkenyloxy" refers to —O-(substituted cycloalkenyl).

"Cycloalkenylthio" refers to —S-cycloalkenyl. In other embodiments, sulfur may be oxidized to sulfinyl or sulfonyl moieties. The sulfoxide may exist as one or more stereoisomers.

"Substituted cycloalkenylthio" refers to —S-(substituted cycloalkenyl). In other embodiments, sulfur may be oxidized to —S(O)— or —$SO_2$— moieties. The sulfoxide may exist as one or more stereoisomers.

"Guanidino" refers to the group —NHC(=NH)$NH_2$.

"Substituted guanidino" refers to the group —$NR^{33}$C(=$NR^{33}$)N($R^{33}$)$_2$, wherein each $R^{33}$ independently is selected from the group consisting of hydrogen, alkyl, substituted alkyl, aryl, substituted aryl, heteroaryl, substituted heteroaryl, heterocyclic, and substituted heterocyclic; two R groups attached to a common guanidino nitrogen atom are optionally joined together with the nitrogen bound thereto to form a heterocyclic or substituted heterocyclic group, provided that at least one R is not hydrogen; and said substituents are as defined herein.

"Halo" or "halogen" refers to fluoro, chloro, bromo, and iodo and is preferably fluoro or chloro.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen, and sulfur within the ring. Such heteroaryl groups can have a single ring (e.g., pyridinyl or furyl) or multiple condensed rings (e.g., indolizinyl or benzothienyl), wherein the condensed rings may or may not be aromatic and/or contain a heteroatom, provided that the point of attachment is through an atom of the aromatic group containing the heteroatom. In one embodiment, the nitrogen and/or sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 5 substituents selected from the group consisting of the same group of substituents defined for substituted aryl. In some embodiments, the heteroaryl has 1 to 3 of the aforementioned groups. In other embodiments, the heteroaryl has 1 to 2 of the aforementioned groups.

"Heteroaryloxy" refers to —O-heteroaryl.

"Substituted heteroaryloxy" refers to the group —O-(substituted heteroaryl).

"Heteroarylthio" refers to the group —S-heteroaryl. In other embodiments, sulfur may be oxidized to —S(O)— or —SO$_2$— moieties. The sulfoxide may exist as one or more stereoisomers.

"Substituted heteroarylthio" refers to the group —S-(substituted heteroaryl). In other embodiments, sulfur may be oxidized to —S(O)— or —SO$_2$— moieties. The sulfoxide may exist as one or more stereoisomers.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 15 ring atoms, including 1 to 4 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In one embodiment, the nitrogen and/or sulfur atom(s) of the heterocyclic group are optionally oxidized to provide for the N-oxide, —S(O)—, or —SO$_2$— moieties.

"Substituted heterocyclic," "substituted heterocycloalkyl," and "substituted heterocyclyl" refer to heterocyclyl groups that are substituted with from 1 to 5 of the same substituents as defined for substituted cycloalkyl. In some embodiments, the heterocyclyl has 1 to 3 of the aforementioned groups.

"Heterocyclyloxy" refers to the group —O-heterocyclyl.

"Substituted heterocyclyloxy" refers to the group —O-(substituted heterocycyl).

"Heterocyclylthio" refers to the group —S-heterocycyl. In other embodiments, sulfur may be oxidized to —S(O)— or —SO$_2$— moieties. The sulfoxide may exist as one or more stereoisomers.

"Substituted heterocyclylthio" refers to the group —S-(substituted heterocycyl). In other embodiments, sulfur may be oxidized to —S(O)— or —SO$_2$— moieties. The sulfoxide may exist as one or more stereoisomers.

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

"Nitro" refers to the group —NO$_2$.

"Nitroso" refers to the group —NO.

"Oxo" refers to the atom (=O).

"Sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cylcoalkyl, —SO$_2$-cycloalkenyl, —SO$_2$-substituted cycloalkenyl, —SO$_2$-aryl, —SO$_2$-substituted aryl, —SO$_2$-heteroaryl, —SO$_2$-substituted heteroaryl, —SO$_2$-heterocyclic, and —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes groups such as methyl-SO$_2$—, phenyl-SO$_2$—, and 4-methylphenyl-SO$_2$—.

"Sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cylcoalkyl, —OSO$_2$-cycloalkenyl, —OSO$_2$-substituted cycloalkenyl, —OSO$_2$-aryl, —OSO$_2$-substituted aryl, —OSO$_2$-heteroaryl, —OSO$_2$-substituted heteroaryl, —OSO$_2$-heterocyclic, and —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thiol" refers to the group —SH.

"Thioxo" refers to the group (=S).

"Alkylthio" refers to the group —S-alkyl, wherein alkyl is as defined herein. In other embodiments, sulfur may be oxidized to —S(O)—. The sulfoxide may exist as one or more stereoisomers.

"Substituted alkylthio" refers to the group —S-(substituted alkyl), wherein substituted alkyl is as defined herein. In other embodiments, sulfur may be oxidized to —S(O)—. The sulfoxide may exist as one or more stereoisomers.

"Stereoisomer" and "stereoisomers" refer to compounds that differ in the chirality of one or more stereocenters. Stereoisomers include enantiomers and diastereomers.

"Tautomer" refers to alternate forms of a molecule that differ in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

"Patient" refers to human and non-human animals, especially mammals.

"Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like.

"Prodrug" refers to a derivative of an active 4-pyrimidineamine compound (drug) that may require a transformation under the conditions of use, such as within the body, to release the active 2,4-pyrimidinediamine drug. Prodrugs are frequently, but not necessarily, pharmacologically inactive until converted into the active drug. Prodrugs are typically obtained by masking one or more functional groups in an active 2,4-pyrimidinediamine drug believed to be in part required for activity with a progroup (defined below) to form a promoiety which undergoes a transformation, such as cleavage, under the specified conditions of use to release the functional group, and hence the active 2,4-pyrimidinediamine drug. The cleavage of the promoiety may proceed spontaneously, such as by way of a hydrolysis reaction, or it can be catalyzed or induced by another agent, such as an enzyme, light, an acid or base, or a change of or exposure to a physical or environmental parameter, such as temperature. The agent can be endogenous to the conditions of use, such as an enzyme present in the cells to which the prodrug is administered or the acidic conditions of the stomach, or it can be supplied exogenously.

"Progroup" refers to a type of protecting group that, when used to mask a functional group within an active 2,4-pyrimidinediamine drug to form a promoiety, converts the drug into a prodrug. Progroups are typically attached to the functional group of the drug via bonds that are cleavable under specified conditions of use. Thus, a progroup is that portion of a promoiety that cleaves to release the functional group under the specified conditions of use. As a specific example, an amide promoiety of the formula —NH—C(O)CH$_3$ comprises the progroup —C(O)CH$_3$.

"Pharmaceutically effective amount" and "therapeutically effective amount" refer to an amount of a compound sufficient to treat a specified disorder or disease or one or more of its symptoms and/or to prevent the occurrence of the disease or disorder. In reference to tumorigenic proliferative disorders, a pharmaceutically or therapeutically effective amount comprises an amount sufficient to, among other things, cause the tumor to shrink or decrease the growth rate of the tumor.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water.

"Linker" refers to a moiety that attaches the N2 and/or N4 substituents on the 2,4-pyrimidinediamine to their respective nitrogen atoms, which may be the same or different. The nature of the linkers can vary widely, and can include virtually any combination of atoms or groups useful for spacing one molecular moiety from another. For example, the linker may be an acyclic hydrocarbon bridge (e.g, a saturated or unsaturated alkyleno such as methano, ethano, etheno, propano, prop[1]eno, butano, but[1]eno, but[2]eno, buta[1,3]dieno, and the like), a monocyclic or polycyclic hydrocarbon bridge (e.g., [1,2]benzeno, [2,3]naphthaleno, and the like), a simple acyclic heteroatomic or heteroalkyldiyl bridge (e.g., —O—, —S—, —S—O—, —NH—, —PH—, —C(O)—, —C(O)NH—, —S(O)—, —S(O)$_2$—, —S(O)NH—, —S(O)$_2$NH—, —O—CH—, —CH$_2$—O—CH$_2$—, —O—CH═CH—CH$_2$—, and the like), a monocyclic or polycyclic heteroaryl bridge (e.g., [3,4]furano, pyridino, thiopheno, piperidino, piperazino, pyrazidino, pyrrolidino, and the like) or combinations of such bridges. The linkers may be further substituted with one or more of the same or different substituent groups. The nature of these substituent groups may vary broadly. Non-limiting examples of suitable substituent groups include branched, straight-chain or cyclic alkyls, mono- or polycyclic aryls, branched, straight-chain or cyclic heteroalkyls, mono- or polycyclic heteroaryls, halos, branched, straight-chain or cyclic haloalkyls, hydroxyls, oxos, thioxos, branched, straight-chain or cyclic alkoxys, branched, straight-chain or cyclic haloalkoxys, trifluoromethoxys, mono- or polycyclic aryloxys, mono- or polycyclic heteroaryloxys, ethers, alcohols, sulfides, thioethers, sulfanyls (thiols), imines, azos, azides, amines (primary, secondary and tertiary), nitriles (any isomer), cyanates (any isomer), thiocyanates (any isomer), nitrosos, nitros, diazos, sulfoxides, sulfonyls, sulfonic acids, sulfamides, sulfonamides, sulfamic esters, aldehydes, ketones, carboxylic acids, esters, amides, amidines, formadines, amino acids, acetylenes, carbamates, lactones, lactams, glucosides, gluconurides, sulfones, ketals, acetals, thioketals, oximes, oxamic acids, oxamic esters, etc., and combinations of these groups. Substituent groups bearing reactive functionalities may be protected or unprotected, as is well-known in the art.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, Protective Groups in Organic Chemistry, 3.sup.rd Ed., 1999, John Wiley & Sons, NY and Harrison et al., Compendium of Synthetic Organic Methods, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated or alkylated such as benzyl and trityl ethers, as well as alkyl ethers, tetrahydropyranyl ethers, trialkylsilyl ethers (e.g., TMS or TIPPS groups) and allyl ethers.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups are limited to -substituted aryl-(substituted aryl)-substituted aryl.

Similarly, it is understood that the above definitions are not intended to include impermissible substitution patterns (e.g., methyl substituted with 5 fluoro groups). Such impermissible substitution patterns are easily recognized by a person having ordinary skill in the art.

C. Methods of Treating Cardiovascular Disorders

This invention provides novel methods of treating cardiovascular disorders, in particular inflammation-related cardiovascular disorders, including, without limitation, atherosclerosis and cardiomyopathy utilizing Syk kinase inhibitors and 2,4-pyrimidinediamine compounds and prodrugs of the compounds. Given the severity of and suffering caused by atherosclerosis, it is vital that new treatments are developed to treat these conditions.

In another aspect, disclosed are methods for treating neurological disorders, in particular neurodegenerative and autoimmune-associated neurological disorders. Examples of neurodegenerative and autoimmune-associated disorders that can be treated according to the present methods include, without limitation, stiff person syndrome, Guillain-Barré syndrome, paraneoplastic neurological disorders, movement disorders (such as arising from Sydenham's chorea), amyotrophic lateral sclerosis, Alzheimer's disease, Parkinson's disease.

Active 2,4-pyrimidinediamine compounds of the invention inhibit Fc receptor signaling cascades that lead to, among other things, degranulation of mast cells and platelets. As a specific example, the compounds inhibit the FcεRI and/or FcγR signal cascades that lead to degranulation of immune cells such as mast cells. Both mast cells and platelets play a central role in the development and progression of atherosclerosis. Upon activation, the IgE receptor signal transduction pathway is activated, which leads to degranulation of the cells and consequent release and/or synthesis of a host of chemical mediators, including histamine, proteases (e.g., tryptase and chymase), lipid mediators such as leukotrienes (e.g., LTC4), platelet-activating factor (PAP) and prostaglandins (e.g., PGD2) and a series of cytokines, including TNF-a, IL-4, IL-13, IL-5, IL-6, IL-8, GMCSF, VEGF and TGF-β. The release and/or synthesis of these mediators from mast cells can lead to degradation of the extracellular matrix, deposition of fatty streaks in the vasculature and rupture of existing atherosclerotic plaques.

The molecular events in the Fc receptor signal transduction pathway that lead to release of preformed mediators via degranulation and release and/or synthesis of other chemical mediators are well-known and are illustrated in FIG. 1. Referring to FIG. 1, the Fc receptor is a heterotetrameric receptor composed of an Ig-binding alpha-subunit, a beta subunit, and two gamma subunits (gamma homodimer). Cross-linking of antibody-bound Fc receptors induces the rapid association and activation of the Src-related kinase Lyn. Lyn phosphorylates immunoreceptor tyrosine-based activation motifs (ITAMS) on the intracellular beta and gamma subunits, which leads to the recruitment of additional Lyn to the beta subunit and Syk kinase to the gamma homodimer. These receptor-associated kinases, which are activated by intra- and intermolecular phosphorylation, phosphorylated other components of the pathway, such as the Btk kinase, LAT, and phospholipase C-gamma PLC-gamma). Activated PLC-gamma initiates pathways that lead to protein kinase C activation and Ca2+ mobilization, both of which are required for degranulation. FcERI cross-linking also activates the three major classes of mitogen activated protein (MAP) kinases, i.e. ERKI/2, JNKI/2, and p38. Activation of these pathways is important in the transcriptional regulation of proinflammatory mediators, such as TNF-α and IL-6, as well as the lipid mediator leukotriene CA (LTC4). Although not illustrated, the FcγR signaling cascade is believed to share some common elements with the FcεRI signaling cascade. Importantly, like FcεRI, the FcγRI includes a gamma homodimer that is phosphorylated and recruits Syk, and like FcεRI, activation of the FcγRI signaling cascade leads to, among other things, degranulation. Other Fc receptors that share the gamma homodimer, and which can be regulated by the active 2,4-pyrimidinediamine compounds include, but are not limited to, FcaRI and FcγIII.

The ability of the 2,4-pyrimidinediamine compounds of the invention to inhibit Fc receptor signaling cascades may be simply determined or confirmed in in vitro assays. Suitable assays for confirming inhibition of FcεRI mediated degranulation are provided in the Examples section. In one typical assay, cells capable of undergoing FcεRI-mediated degranulation, such as mast or basophil cells, are first grown in the presence of IL-4, Stem Cell Factor (SCF), IL-6 and IgE to increase expression of the FcεRI, exposed to a 2,4-pyrimidinediamine test compound of the invention and stimulated with anti-IgE antibodies (or, alternatively, an IgE-specific allergen). Following incubation, the amount of a chemical mediator or other chemical agent released and/or synthesized as a consequence of activating the FcεRI signaling cascade may be quantified using standard techniques and compared to the amount of the mediator or agent released from control cells (i.e., cells that are stimulated but that are not exposed to test compound). The concentration of test compound that yields a 50% reduction in the quantity of the mediator or agent measured as compared to control cells is the $IC_{50}$ of the test compound. The origin of the mast or basophil cells used in the assay will depend, in part, on the desired use for the compounds and will be apparent to those of skill in the art. For example, if the compounds will be used to treat or prevent a particular disease in humans, a convenient source of mast or basophil cells is a human or other animal which constitutes an accepted or known clinical model for the particular disease. Thus, depending upon the particular application, the mast or basophil cells may be derived from a wide variety of animal sources, ranging from, for example, lower mammals such as mice and rats, to dogs, sheep and other mammals commonly employed in clinical testing, to higher mammals such as monkeys, chimpanzees and apes, to humans. Specific examples of cells suitable for carrying out the in vitro assays include, but are not limited to, rodent or human basophil cells, rat basophil leukemia cell lines, primary mouse mast cells (such as bone marrow-derived mouse mast cells "BMMC") and primary human mast cells isolated from cord blood ("CHMC") or other tissues such as lung. Methods for isolating and culturing these cell types are well-known (see, e.g., Demo et al., 1999, Cytometry 36(4):340-348 and U.S. Pat. No. 7,060,827, the disclosures of which are incorporated herein by reference). Of course, other types of immune cells that degranulate upon activation of the FcεRI signaling cascade may also be used, including, for example, eosinophils.

Accordingly, the activity of the 2,4-pyrimidinediamine compounds of the invention may also be confirmed in biochemical or cellular assays of Syk kinase activity. In the FcεRI signaling cascade in mast and/or basophil cells, Syk kinase phosphorylates LAT and PLC-gamma1, which leads to, among other things, degranulation. Any of these activities may be used to confirm the activity of an anti-atherosclerotic compounds of the invention. In one embodiment, the activity is confirmed by contacting an isolated Syk kinase, or an active fragment thereof with a compound in the presence of a Syk kinase substrate (e.g., a synthetic peptide or a protein that is known to be phosphorylated by Syk in a signaling cascade) and assessing whether the Syk kinase phosphorylated the substrate. Alternatively, the assay may be carried out with cells that express a Syk kinase. The cells may express the Syk kinase endogenously or they may be engineered to express a recombinant Syk kinase. The cells may optionally also express the Syk kinase substrate. Cells suitable for performing such confirmation assays, as well as methods of engineering suitable cells will be apparent to those of skill in the art. Specific examples of biochemical and cellular assays suitable for confirming the activity of a Syk inhibitor are provided in the Examples section. Generally, compounds that are Syk kinase inhibitors will exhibit an $IC_{50}$ with respect to a Syk kinase activity, such as the ability of Syk kinase to phosphorylate a synthetic or endogenous substrate, in an in vitro or cellular assay in the range of about 20 μM or less. Skilled artisans will appreciate that compounds that exhibit lower IC50s, such as in the range of 10 μM, 1 μM, 100 nM, 10 nM, 1 nM, or even lower, are particularly useful.

Preferred Syk kinase inhibitors for use in the methods of the invention include compounds of structural formula I:

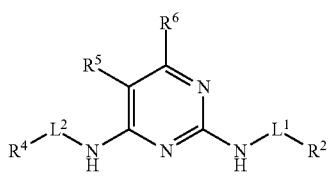

I wherein:
- $L^1$ and $L^2$ are each, independently of one another, selected from the group consisting of a direct bond and a linker;
- $R^2$ is selected from the group consisting of $C_{1-6}$ alkyl optionally substituted with one or more of the same or different $R^8$ groups, $C_{3-8}$ cycloalkyl optionally substituted with one or more of the same or different $R^8$ groups, cyclohexyl optionally substituted with one or more of the same or different $R^8$ groups, 3-8 membered cycloheteroalkyl optionally substituted with one or more of the same or different $R^8$ groups, $C_{5-15}$ aryl optionally substituted with one or more of the same or different $R^8$ groups, phenyl optionally substituted with one or more of the same or different $R^8$ groups and 5-15 membered heteroaryl optionally substituted with one or more of the same or different $R^8$ groups;
- $R^4$ is selected from the group consisting of hydrogen, $C_{1-6}$ alkyl optionally substituted with one or more of the same or different $R^8$ groups, $C_{3-8}$ cycloalkyl optionally substituted with one or more of the same or different $R^8$ groups, 3-8 membered cycloheteroalkyl optionally substituted with one or more of the same or different $R^8$ groups, $C_{5-15}$ aryl optionally substituted with one or more of the same or different $R^8$ groups, and 5-15 membered heteroaryl optionally substituted with one or more of the same or different $R^8$ groups;
- $R^5$ is selected from the group consisting of $R^6$, $C_{1-6}$ alkyl optionally substituted with one or more of the same or different $R^8$ groups;
- each $R^6$ is independently selected from the group consisting of hydrogen, an electronegative group, —$OR^d$, —$SR^d$, $C_{1-3}$ haloalkyloxy, $C_{1-3}$ perhaloalkyloxy, —$NR^cR^c$, halogen, $C_{1-3}$ haloalkyl, $C_{1-3}$ perhaloalkyl, —$CF_3$, —$CH_2CF_3$, —$CF_2CF_3$, —CN, —NC, —OCN, —SCN, —NO, —$NO_2$, —$N_3$, —$S(O)R^d$, —$S(O)_2R^d$, —$S(O)_2OR^d$, —$S(O)NR^cR^c$, —$S(O)_2NR^cR^c$, —$OS(O)R^d$, —$OS(O)_2R^d$, —$OS(O)_2OR^d$, —$OS(O)NR^cR^c$, —$OS(O)_2NR^cR^c$, —$C(O)R^d$, —$C(O)OR^d$, —$C(O)NR^cR^c$, —$C(NH)NR^cR^c$, —$OC(O)R^d$, —$SC(O)R^d$, —$OC(O)OR^d$, —$SC(O)OR^d$, —$OC(O)NR^cR^c$,
—$SC(O)NR^cR^c$, —$OC(NH)NR^cR^c$, —$SC(NH)NR^cR^c$, —[$NHC(O)]_nR^d$, —[$NHC(O)]_nOR^d$, —[NHC(O)]_nNR^cR^c$ and —[NHC(NH)]_nNR^cR^c$, $C_{5-10}$ aryl optionally substituted with one or more of the same or different $R^8$ groups, $C_{6-16}$ arylalkyl optionally substituted with one or more of the same or different $R^8$ groups, 5-10 membered heteroaryl optionally substituted with one or more of the same or different $R^8$ groups and 6-16 membered heteroarylalkyl optionally substituted with one or more of the same or different $R^8$ groups;
- $R^8$ is selected from the group consisting of $R^e$, $R^b$, $R^e$ substituted with one or more of the same or different $R^a$ or $R^b$, —$OR^a$ substituted with one or more of the same or different $R^a$ or $R^b$, —$B(OR^a)_2$, —$B(NR^cR^c)_2$, —$(CH_2)_m$—$R^b$, —$(CHR^a)_m$—$R^b$, —O—$(CH_2)_m$—$R^b$, $S(CH_2)_m$—$R^b$, —O—$CHR^aR^b$, —O—$CR^a(R^a)_2$, —O—$(CHR^a)_m$—$R^b$, —O—$(CH_2)_m$—$CH[(CH_2)_mR^b]R^b$, —S—$(CHR^a)_m$—$R^b$; —$C(O)NH$—$(CH_2)_m$—$R^b$, —$C(O)NH$—$(CHR^a)_m$—$R^b$, —$O(CH_2)_m$—$C(O)NH$—$(CH_2)_m$—$R^b$, —S—$(CH_2)_m$—$R^b$, —$C(O)NH$—$(CH_2)_mR^b$, —O—$(CHR^a)_m$—$C(O)NH$—$(CHR^a)_m$—$R^b$, —S—$(CHR^a)_m$—$C(O)NH$—$(CHR^a)_m$—$R^b$, —NH—$(CH_2)_m$—$R^b$, —NH—$(CHR^a)_m$—$R^b$, —NH[$(CH_2)_mR^b$], —N[$(CH_2)_mR^b]_2$, —NH—$C(O)$—NH—$(CH_2)_m$—$R^b$, —NH—$C(O)$—$(CH_2)_m$—$CHR^bR^b$ and —NH—$(CH_2)_m$—$C(O)$—NH—$(CH_2)_m$—$R^b$;
- each $R^a$ is independently selected from the group consisting of hydrogen, $C_{1-6}$ alkyl, $C_{3-8}$ cycloalkyl, $C_{4-11}$ cycloalkylalkyl, $C_{5-10}$ aryl, $C_{6-16}$ arylalkyl, 2-6 membered heteroalkyl, 3-8 membered cycloheteroalkyl, 4-11 membered cycloheteroalkylalkyl, 5-10 membered heteroaryl and 6-16 membered heteroarylalkyl;
- each $R^b$ is independently selected from the group consisting of =O, —$OR^d$, (C1-C3) haloalkyloxy, —$OCF_3$, =S, —$SR^d$, =$NR^d$, =$NOR^d$, —$NR^cR^c$, halogen, —$CF_3$, —CN, —NC, —OCN, —SCN, —NO, —$NO_2$, =$N_2$, —$N_3$, —$S(O)R^d$, —$S(O)_2R^d$, —$S(O)_2OR^d$, —$S(O)NR^cR^c$, —$S(O)_2NR^cR^c$, —$OS(O)R^d$, —$OS(O)_2R^d$, —$OS(O)_2OR^d$, —$OS(O)_2NR^cR^c$, —$C(O)R^d$, —$C(O)OR^d$, —$C(O)NR^cR^c$, —$C(NH)NR^cR^c$, —$C(NR^a)NR^cR^c$, —$C(NOH)R^a$, —$C(NOH)NR^cR^c$, —$OC(O)R^d$, —$OC(O)OR^d$, —$OC(O)NR^cR^c$, —$OC(NH)NR^cR^c$, —$OC(NR^a)NR^cR^c$, —[$NHC(O)]_nR^d$, —[$NR^aC(O)]_nR^d$, —[$NHC(O)]_nOR^d$, —[$NR^aC(O)]_nOR^d$, —[$NHC(O)]_nNR^cR^c$, —[$NR^aC(O)]_nNR^cR^c$, —[$NHC(NH)]_nNR^cR^c$ and —[$NR^aC(NR^a)]_nNR^cR^c$;
- each $R^c$ is independently a protecting group or $R^a$, or, alternatively, each $R^c$ is taken together with the nitrogen atom to which it is bonded to form a 5 to 8-membered cycloheteroalkyl or heteroaryl which may optionally include one or more of the same or different additional heteroatoms and which may optionally be substituted with one or more of the same or different $R^a$ or $R^b$ groups;
- each $R^d$ is independently a protecting group or $R^a$;
- each $R^e$ is independently selected from the group consisting of $C_{1-6}$ alkyl, $C_{3-8}$ cycloalkyl, $C_{4-11}$ cycloalkylalkyl, $C_{5-10}$ aryl, $C_{6-16}$ arylalkyl, 2-6 membered heteroalkyl, 3-8 membered cycloheteroalkyl, 4-11 membered cycloheteroalkylalkyl, 5-10 membered heteroaryl and 6-16 membered heteroarylalkyl;
- each m is independently an integer from 1 to 3; and
- each n is independently an integer from 0 to 3.

In a preferred implementation, $R^6$ is hydrogen and each of $L^1$ and $L^2$ is a direct bond. More preferably, $R^5$ is selected from the group consisting of halo, —CN, —$NO_2$, —$C(O)R^a$, —$C(O)ORa$, —$C(O)CF_3$, —$C(O)OCF_3$, $C_{1-3}$ haloalkyl, $C_{1-3}$ perhaloalkyl, $C_{1-3}$ haloalkoxy, $C_{1-3}$ perhaloalkoxy, —OCF$_3$ and —CF$_3$. In a particularly preferred implementation, R$^5$ is fluoro. In yet another implementation, R$^2$ is selected from the group consisting of phenyl, naphthyl, and 5-10 membered heteroaryl, optionally substituted with one or more of the same or different R$^8$ groups. Preferably R$^2$ is selected from the group consisting of benzodioxanyl, 1,4-benzodioxan-(5 or 6)-yl, benzodioxolyl, 1,3-benzodioxol-(4 or 5)-yl, benzoxazinyl, 1,4-benzoxazin-(5, 6, 7 or 8)-yl, benzoxazolyl, 1,3-benzoxazol-(4, 5, 6 or 7)-yl, benzopyranyl, benzopyran-(5, 6, 7 or 8)-yl, benzotriazolyl, benzotrazol-(4, 5, 6 or 7)-yl, 1,4-benzoxazinyl-2-one, 1,4-benzoxazin-(5, 6, 7 or 8)-yl-2-one, 2H-1,4-benzoxazinyl-3(4H)-one, 2H-1,4-benzoxazin-(5, 6, 7 or 8)-yl-3(4H)-one, 2H-1,3-benzoxazinyl-2,4(3H)-dione, 2H-1,3-benzoxazin-(5, 6, 7 or 8)-yl-2,4(3H)-dione, benzoxazolyl-2-one, benzoxazol-(4, 5, 6 or 7)-yl-2-one, dihydrocoumarinyl, dihydrocoumarin-(5, 6, 7 or 8)-yl, 1,2-benzopyronyl, 1,2-benzopyron-(5, 6, 7 or 8)-yl, benzofuranyl, benzofuran-(4, 5, 6 or 7)-yl, benzo[b]furanyl, benzo[b]furan-(4, 5, 6, or -7)-yl, indolyl, indol-(4, 5, 6 or 7)-yl, pyrrolyl and pyrrol-(1 or 2)-yl, optionally substituted with one or more of the same of different R$^8$ groups.

In one implementation of the invention, one or both of R$^2$ and R$^4$ are, independently of one another, is a heteroaryl selected from the group consisting of:

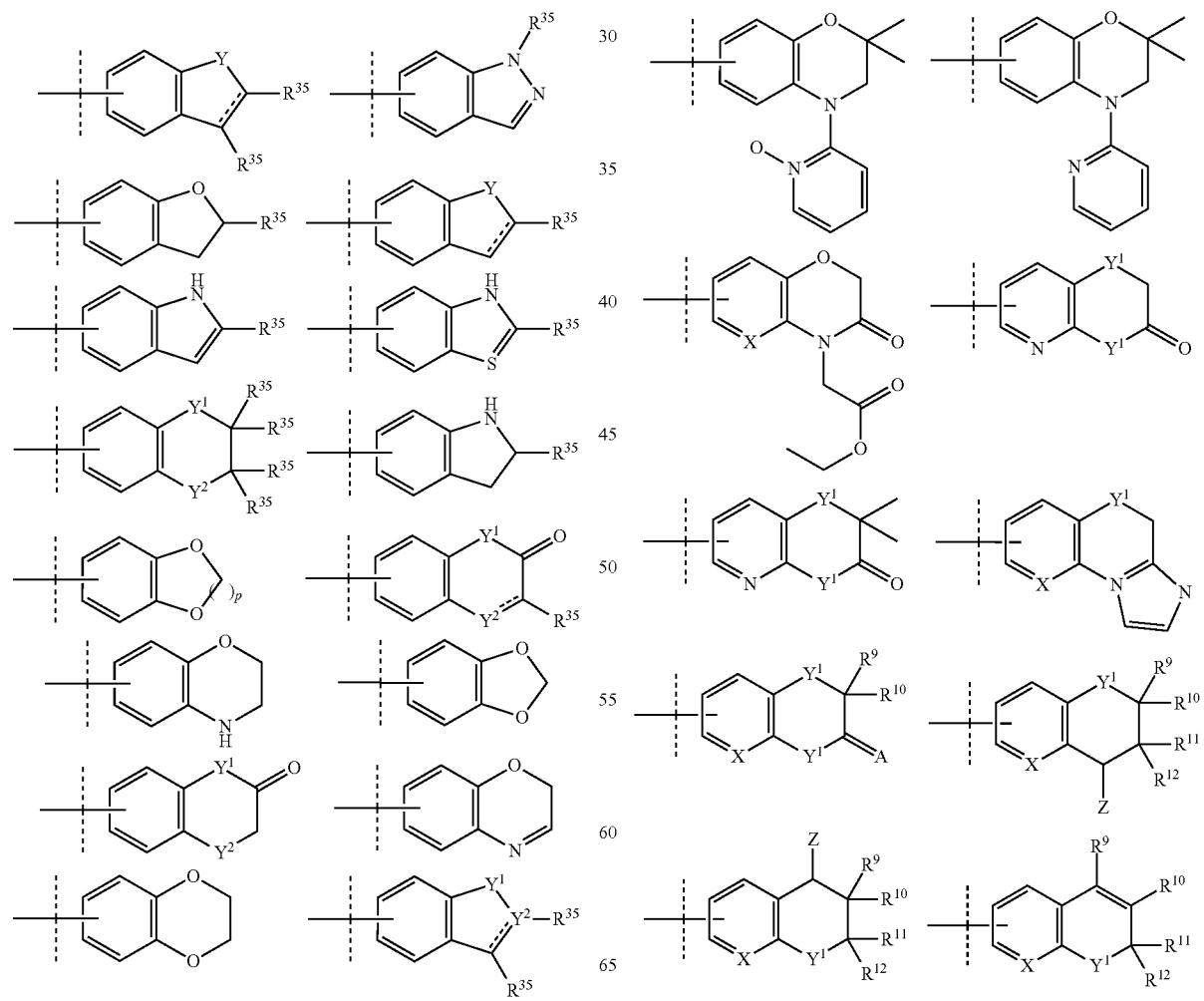

-continued

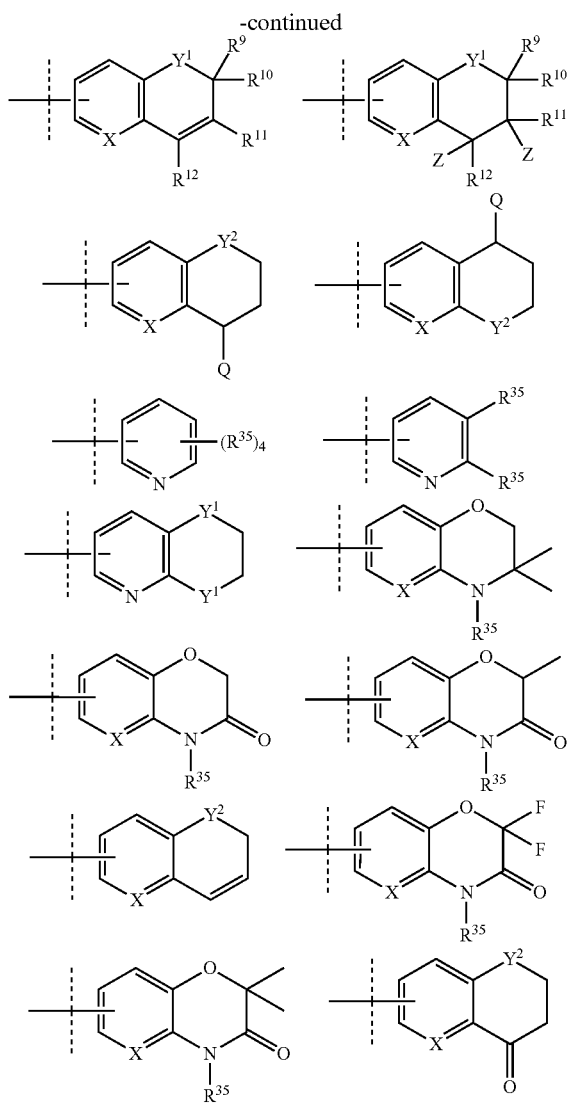

wherein:
p is an integer from one to three;
each - - - independently represents a single bond or a double bond;
$R^{35}$ is hydrogen or $R^8$;
X is selected from the group consisting of CH, N and N—O;
each Y is independently selected from the group consisting of O, S and NH;
each $Y^1$ is independently selected from the group consisting of O, S, SO, $SO_2$, $SONR^{36}$, NH and $NR^{37}$;
each $Y^2$ is independently selected from the group consisting of CH, $CH_2$, O, S, N, NH and $NR^{37}$;
$R^{36}$ is hydrogen or alkyl;
$R^{37}$ is selected from the group consisting of hydrogen and a progroup,
$R^{38}$ is selected from the group consisting of alkyl and aryl;
A is selected from the group consisting of O, NH and $NR^{38}$;
$R^9$, $R^{10}$, $R^{11}$ and $R^{12}$ are each, independently of one another, selected from the group consisting of alkyl, alkoxy, halogen, haloalkoxy, aminoalkyl and hydroxyalkyl, or, alternatively, $R^9$ and $R^{10}$ or $R^{11}$ and $R^{12}$, or $R^9$ and $R^{10}$ and $R^{11}$ and $R^{12}$ are taken together form an oxo group;

each Z is selected from the group consisting of hydroxyl, alkoxy, aryloxy, ester, and carbamate;
Q is selected from the group consisting of —OH, $OR^8$, —$NR^cR^c$, —$NHR^{39}$—$C(O)R^8$, —$NHR^{39}$—$C(O)OR^8$, —$NR^{39}$—$CHR^{40}$—$R^b$, —$NR^{39}$—$(CH_2)_m$—$R^b$ and —$NR^{39}$—$C(O)$—$CHR^{40}$—$NR^cR^c$; and
$R^{39}$ and $R^{40}$ are each, independently of one another, selected from the group consisting of hydrogen, alkyl, aryl, alkylaryl, arylalkyl and $NHR^8$.

In a preferred implementation, $R^2$ is phenyl substituted with one or more $R^8$ groups. More preferably, $R^2$ is phenyl substituted with one to three alkoxy groups.

In another preferred implementation, $R^4$ is

One aspect of the invention provides methods of treating atherosclerosis or regressing or decreasing formation of arterial atherosclerotic lesions, said method comprising administering to a mammal having atherosclerosis an effective amount of a compound of formula III:

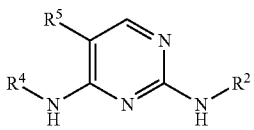

III wherein each of $R^2$ and $R^4$ independently is phenyl substituted with one or more $R^8$ groups or a heteroaryl selected from the group consisting of

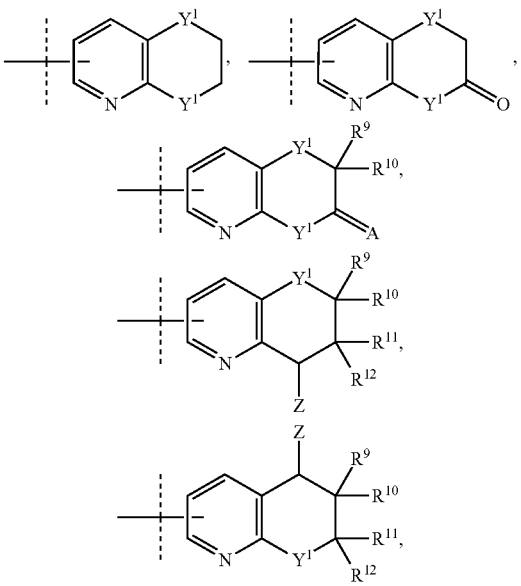

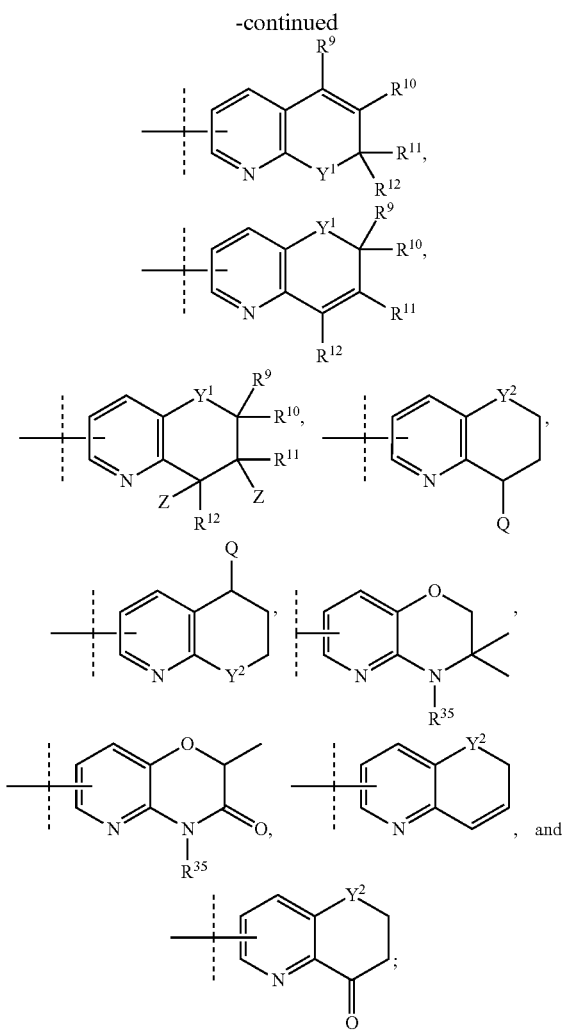

wherein:

R$^{35}$ is hydrogen or R$^8$;

R$^8$ is R$^e$, R$^b$, R$^e$ substituted with one or more of the same or different R$^a$ or R$^b$, —OR$^a$ substituted with one or more of the same or different R$^a$ or R$^b$, —B(OR$^a$)$_2$, —B(NR$^c$R$^c$)$_2$, —(CH$_2$)$_m$—R$^b$, —(CHR$^a$)$_m$—R$^b$, —O—(CH$_2$)$_m$—R$^b$, —S—(CH$_2$)$_m$—R$^b$, —O—CHR$^a$R$^b$, —O—CR$^a$(R$^b$)$_2$, —O—(CHR$^a$)$_m$—R$^b$, —O—(CH$_2$)$_m$—CH[(CH$_2$)$_m$R$^b$]R$^b$, —S—(CHR$^a$)$_m$—R$^b$, —C(O)NH—(CH$_2$)$_m$—R$^b$, —C(O)NH—(CHR$^a$)$_m$—R$^b$, —O—(CH$_2$)$_m$—C(O)NH—(CH$_2$)$_m$—R$^b$, —S—(CH$_2$)$_m$—C(O)NH—(CH$_2$)$_m$—R$^b$, —O—(CHR$^a$)$_m$—C(O)NH—(CHR$^a$)$_m$—R$^b$, —S—(CHR$^a$)$_m$—C(O)NH—(CHR$^a$)$_m$—R$^b$, —NH—(CH$_2$)$_m$—R$^b$, —NH—(CHR$^a$)$_m$—R$^b$, —NH[(CH$_2$)$_m$R$^b$], —N[(CH$_2$)$_m$R$^b$]$_2$, —NH—C(O)—NH—(CH$_2$)$_m$—R$^b$, —NH—C(O)—(CH$_2$)$_m$—CHR$^b$R$^b$ or —NH—(CH$_2$)$_m$—C(O)—NH—(CH$_2$)$_m$—R$^b$;

each R$^a$ is independently selected from the group consisting of hydrogen, (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl and 6-16 membered heteroarylalkyl;

each R$^b$ is independently selected from the group consisting of =O, —OR$^d$, (C1-C3) haloalkyloxy, —OCF$_3$, =S, —SR$^d$, =NR$^d$, =NOR$^d$, —NR$^c$R$^c$, halogen, —CF$_3$, —CN, —NC, —OCN, —SCN, —NO, —NO$_2$, =N$_2$, —N$_3$, —S(O)R$^d$, —S(O)$_2$R$^d$, —S(O)$_2$OR$^d$, —S(O)NR$^c$R$^c$, —S(O)$_2$NR$^c$R$^c$, —OS(O)R$^d$, —OS(O)$_2$R$^d$, —OS(O)$_2$OR$^d$, —OS(O)$_2$NR$^c$R$^c$, —C(O)R$^d$, —C(O)OR$^d$, —C(O)NR$^c$R$^c$, —C(NH)NR$^c$R$^c$, —C(NR$^a$)NR$^c$R$^c$, —C(NOH)R$^a$, —C(NOH)NR$^c$R$^c$, —OC(O)R$^d$, —OC(O)OR$^d$, —OC(O)NR$^c$R$^c$, —OC(NH)NR$^c$R$^c$, —OC(NR$^a$)NR$^c$R$^c$, —[NHC(O)]$_n$R$^d$, —[NR$^a$C(O)]$_n$R$^d$, —[NHC(O)]$_n$OR$^d$, —[NR$^a$C(O)]$_n$OR$^d$, —[NHC(O)]$_n$NR$^c$R$^c$, —[NR$^a$C(O)]$_n$NR$^c$R$^c$, —[NHC(NH)]$_n$NR$^c$R$^c$ and —[NR$^a$C(NR$^a$)]$_n$NR$^c$R$^c$;

each R$^c$ is independently a protecting group or R$^a$, or, alternatively, two R$^c$ are taken together with the nitrogen atom to which they are bonded to form a 5 to 8-membered cycloheteroalkyl or heteroaryl which may optionally include one or more of the same or different additional heteroatoms and which may optionally be substituted with one or more of the same or different R$^a$ or R$^b$ groups;

each R$^d$ is independently a protecting group or R$^a$;

each R$^e$ is independently selected from the group consisting of (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl and 6-16 membered heteroarylalkyl;

X is selected from the group consisting of CH, N and N—O;

each Y independently is selected from the group consisting of O, S and NH;

each Y$^1$ independently is selected from the group consisting of O, S, SO, SO$_2$, SONR$^{36}$, NH and NR$^{35}$;

each Y$^2$ independently is selected from the group consisting of CH, CH$_2$, O, S, N, NH and NR$^{35}$;

each R$^{36}$ independently is hydrogen or alkyl;

A is selected from the group consisting of O, NH and NR$^{38}$;

Q is selected from the group consisting of —OH, OR$^8$, —NR$^c$R$^c$, NHR$^{39}$C(O)R$^8$, —NHR$^{39}$—C(O)OR$^8$, —NR$^{39}$—CHR$^{40}$—R$^b$, —NR$^{39}$—(CH$_2$)$_m$—R$^b$ and —NR$^{39}$—C(O)—CHR$^{40}$—NR$^c$R$^c$;

each R$^{38}$ independently is selected from the group consisting of alkyl and aryl;

R$^9$, R$^{10}$, R$^{11}$ and R$^{12}$ are each, independently of one another, selected from the group consisting of alkyl, alkoxy, halogen, haloalkoxy, aminoalkyl and hydroxyalkyl, or, alternatively, R$^9$ and R$^{10}$ or R$^{11}$ and R$^{12}$, or R$^9$ and R$^{10}$ and R$^{11}$ and R$^{12}$ are taken together form an oxo group;

each Z is selected from the group consisting of hydroxyl, alkoxy, aryloxy, ester, and carbamate;

Q is selected from the group consisting of —OH, OR$^8$, —NR$^c$R$^c$, —NHR$^{39}$—C(O)R$^8$, —NHR$^{39}$—C(O)OR$^8$, —NR$^{39}$—CHR$^{40}$—R$^b$, —NR$^{39}$—(CH$_2$)$_m$—R$^b$ and —NR$^{39}$—C(O)—CHR$^{40}$—NR$^c$R$^c$; and R$^{39}$ and R$^{40}$ are each, independently of one another, selected from the group consisting of hydrogen, alkyl, aryl, alkylaryl, arylalkyl and NHR$^8$; and each m independently is an integer from 1 to 3; and each n is independently an integer from 0 to 3.

In certain implementations, the compound administered to the mammal in need thereof is a prodrug of a Syk kinase inhibitor. The prodrugs generally comprise a biologically active 2,4-pyrimidinediamine compound that is substituted at the nitrogen atom of one or more primary or secondary amine groups with a progroup ($R^P$) that metabolizes or otherwise transforms under conditions of use to yield the active 2,4-pyrimidinediamine. In some embodiments, the progroup is a phosphorous-containing progroup. In some embodiments, the progroup includes a group or moiety that is metabolized under the conditions of use to yield an unstable α-hydroxymethyl α-aminomethyl or α-thiomethyl intermediate, which then further metabolized in vivo to yield the active 2,4-pyrimidinediamine drug. In some embodiments, the progroup includes an α-hydroxyalkyl, α-aminoalkyl or α-thioalkyl moiety, for example an α-hydroxymethyl, α-aminomethyl, α-thiomethyl moiety, that metabolizes under the conditions of use to yield the active 2,4 pyrimidinediamine drug. For example, in some embodiments the progroup is of the formula —$(CR^dR^d)_y$-A-$R^3$, where y is 1, 2 or 3, each $R^d$ is, independently of the other, selected from hydrogen, cyano, optionally substituted (C1-C20) alkyl, (C1-C20) perfluoroalkyl, optionally substituted (C7-C30) arylalkyl and optionally substituted 6-30 membered heteroarylalkyl, where each optional substituent is, independently of the others, selected from hydrogen, alkyl, aryl, arylalkyl, heteroaryl and heteroalkyl, or, alternatively, the two $R^d$ are taken together with the carbon atom to which they are bonded to form a cycloalkyl containing from 3 to 8 carbon atoms; A is selected from O, S and $NR^{50}$, where $R^{50}$ is selected from hydrogen, alkyl, aryl, arylalkyl, heteroaryl, heteroarylalkyl and cycloheteroalkyl, or alternatively is combined with $R^3$, and, together with the nitrogen to which they are attached, form a 3-7 membered ring; and $R^3$ represents a group that can be metabolized in vivo to yield a group of the formula —$CR^dR^d$-AH, where $R^d$ and A are as previously defined.

The identity of $R^3$ is not critical, provided that it can be metabolized under the desired conditions of use, for example under the acidic conditions found in the stomach and/or by enzymes found in vivo, to yield a group of the formula —$CR^dR^d$-AH, where A and $R^d$ are as previously defined. Thus, skilled artisans will appreciate that $R^3$ can comprise virtually any known or later-discovered hydroxyl, amine or thiol protecting group. Non-limiting examples of suitable protecting groups can be found, for example, in Protective Groups in Organic Synthesis, Greene & Wuts, 2nd Ed., John Wiley & Sons, New York, 1991 (especially pages 10-142 (alcohols, 277-308 (thiols) and 309-405 (amines) the disclosure of which is incorporated herein by reference).

In a specific embodiment, $R^3$ includes, together with A, an ether, a thioether, a silyl ether, a silyl thioether, an ester, a thioester, an amide, a carbonate, a thiocarbonate, a carbamate, a thiocarbamate, or a urea linkage, —$OCH_2SO_3R$, where R is hydrogen, alkyl, aryl, arylalkyl or a metal salt (e.g., sodium, lithium, potassium); -$GCH_2N^+(R^{51})_3M^-$, where G is absent, —$OPO_3^-$, $OSO_3^-$ or —$CO_2^-$, $R^{51}$ is hydrogen, alkyl, aryl, arylalkyl, cycloheteroalkyl or cycloheteroalkylalkyl and M- is a counterion, usually a halide ion or the like (acetate, sulfate, phosphate, etc.). Specific exemplary embodiments include, but are not limited to, progroups $R^P$ in which $R^3$ is selected from $R^f$, —C(O)$R^f$, —C(O)O$R^f$, —C(O)N$R^fR^f$ and —Si$R^fR^fR^f$, where each $R^f$ is, independently of the others, selected from hydrogen, optionally substituted lower alkyl, optionally substituted lower heteroalkyl, optionally substituted lower cycloalkyl, optionally substituted lower heterocycloalkyl, optionally substituted (C6-C10) aryl, optionally substituted 5-10 membered heteroaryl, optionally substituted (C7-C18) arylalkyl and optionally substituted 6-18 membered heteroarylalkyl. In a specific embodiment, each $R^f$ is the same.

The identity of the progroup(s) can be selected to tailor the water-solubility and other properties of the underlying active 2,4-pyrimidinediamine compound to be optimized for a particular mode of administration. It can also be selected to provide for removal at specified organs and/or tissues within the body, such as, for example, in the digestive tract, in blood and/or serum, or via enzymes residing in specific organs, such as the liver.

In some embodiments, progroups that are phosphorous-containing progroups include phosphate moieties that can be cleaved in vitro by enzymes such as esterases, lipases and/or phosphatases. Such enzymes are prevalent throughout the body, residing in, for example, the stomach and digestive tract, blood and/or serum, and in virtually all tissues and organs. Such phosphate-containing progroups will generally increase the water-solubility of the underlying active 2,4-pyrimidinediamine compound, making such phosphate-containing prodrugs ideally suited for modes of administration where water-solubility is desirable, such as, for example, oral, buccal, intravenous, intramuscular and ocular modes of administration.

In some embodiments, each phosphate-containing progroup in the prodrug is of the formula —$(CR^dR^d)_y$—O—P(O)(OH)(OH), or a salt thereof, wherein y and $R^d$ are as previously defined. In one specific embodiment, each $R^d$ is, independently of the others, selected from the group consisting of hydrogen, substituted or unsubstituted lower alkyl, substituted or unsubstituted phenyl, substituted or unsubstituted methyl and substituted or unsubstituted benzyl. In another specific embodiment, each $R^d$ is, independently of the others, selected from the group consisting of hydrogen and unsubstituted lower alkyl. Specific exemplary phosphate-containing progroups RP include —$CH_2$—O—P(O)(OH)(OH) and —$CH_2CH_2$—O—P(O)(OH)(OH) and/or the corresponding salts.

A preferred prodrug for use in the methods of the invention includes compounds of structural formula II:

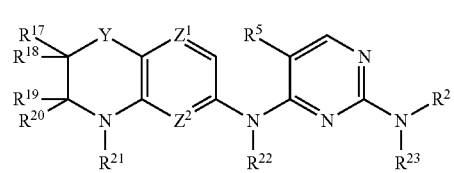

wherein:
Y is selected from $CH_2$, $NR^{24}$, O, S, S(O) and $S(O)_2$;
$Z^1$ and $Z^2$ each, independently of one another, are selected from CH and N;
$R^2$ is selected from the group consisting of (CI-C6) alkyl optionally substituted with one or more of the same or different $R^8$ groups, (C3-C8) cycloalkyl optionally substituted with one or more of the same or different $R^8$ groups, 3-8 membered cycloheteroalkyl optionally substituted with one or more of the same or different $R^8$ groups, (C6-C14) aryl optionally substituted with one or more of the same or different $R^8$ groups, and 5-15 membered heteroaryl optionally substituted with one or more of the same or different $R^8$ groups;
$R^5$ is selected from halo, cyano, nitro, and trihalomethyl;
$R^8$ is selected from the group consisting of $R^a$, $R^b$, $R^a$ substituted with one or more of the same or different $R^a$ or $R^b$, —$OR^a$ substituted with one or more of the same or different $R^a$ or $R^b$, —$B(OR^a)_2$, —$B(NR^cR^c)_2$, —$(CH_2)_m$—$R^b$, —$(CHR^a)_m$—$R^b$, —O—$(CH_2)_m$—$R^b$, —S—(CH$_2$)$_m$—R$^b$, —O—CHR$^a$R$^b$, —O—CR$^a$(R$^b$)$_2$, —O—(CHR$^a$)$_m$—R$^b$, —O—(CH$_2$)$_m$—CH[(CH$_2$)$_m$R$^b$]R$^b$, —S—(CHR$^a$)$_m$—R$^b$, —C(O)NH—(CH$_2$)$_m$—R$^b$, —C(O)NH—(CHR$^a$)$_m$—R$^b$, —O—(CH$_2$)$_m$—C(O)NH—(CH$_2$)$_m$—R$^b$, —S—(CH$_2$)$_m$—C(O)NH—(CH$_2$)$_m$—R$^b$, —O—(CHR$^a$)$_m$—C(O)NH—(CHR$^a$)$_m$—R$^b$, —S—(CHR$^a$)$_m$—C(O)NH—(CHR$^a$)$_m$—R$^b$, —NH—(CH$_2$)$_m$—R$^b$, —NH—(CHR$^a$)$_m$—R$^b$, —NH[(CH$_2$)$_m$R$^b$], —N[(CH$_2$)$_m$R$^b$]$_2$, —NH—C(O)—NH—(CH$_2$)$_m$—R$^b$, —NH—C(O)—(CH$_2$)$_m$—CHR$^b$R$^b$ and —NH—(CH$_2$)$_m$—C(O)—NH—(CH$_2$)$_m$—R$^b$;

$R^{17}$ is selected from the group consisting of hydrogen, halogen, and lower alkyl or, alternatively, $R^{17}$ may be taken together with $R^{18}$ to form an oxo (=O) group or, together with the carbon atom to which they are attached, a spirocycle containing from 3 to 7 carbon atoms;

$R^{18}$ is selected from the group consisting of hydrogen, halogen, and lower alkyl or, alternatively, $R^{18}$ may be taken together with $R^{17}$ to form an oxo (=O) group or, together with the carbon atom to which they are attached, a spirocycle containing from 3 to 7 carbon atoms;

$R^{19}$ is selected from the group consisting of hydrogen and lower alkyl or, alternatively, $R^{19}$ may be taken together with $R^{20}$ to form an oxo (=O) group or, together with the carbon atom to which they are attached, a spirocycle containing from 3 to 7 carbon atoms;

$R^{20}$ is selected from the group consisting of hydrogen and lower alkyl or, alternatively, $R^{20}$ may be taken together with $R^{19}$ to form an oxo (=O) group or, together with the carbon atom to which they are attached, a spirocycle containing from 3 to 7 carbon atoms;

each $R^a$ is, independently of the others, selected from the group consisting of hydrogen, lower alkyl, lower cycloalkyl, (C4-C11) cycloalkylalkyl, (C6-C10) aryl, (C7-C16) arylalkyl, 2-6 membered heteroalkyl, 3-8 membered cycloheteroalkyl, 4-11 membered cycloheteroalkylalkyl, 5-10 membered heteroaryl and 6-16 membered heteroarylalkyl;

each $R^b$ is independently selected from the group consisting of =O, —OR$^a$, (C1-C3) haloalkyloxy, =S, —SR$^a$, =NR$^a$, =NOR$^a$, —NR$^c$R$^c$, halogen, —CF$_3$, —CN, —NC, —OCN, —SCN, —NO, —NO$_2$, =N$_2$, —N$_3$, —S(O)R$^a$, —S(O)$_2$R$^a$, —S(O)$_2$OR$^a$, —S(O)NR$^c$R$^c$, —S(O)$_2$NR$^c$R$^c$, —OS(O)R$^a$, —OS(O)$_2$R$^a$, —OS(O)$_2$OR$^a$, —OS(O)$_2$NR$^c$R$^c$, —C(O)R$^a$, —C(O)OR$^a$, —C(O)NR$^c$R$^c$, —C(NH)NR$^c$R$^c$, —C(NR$^a$)NR$^c$Rc, —C(NOH)R$^a$, —C(NOH)NR$^c$R$^c$, —OC(O)R$^a$, —OC(O)OR$^a$, —OC(O)NR$^c$R$^c$, —OC(NH)NR$^c$R$^c$, —OC(NR$^a$)NR$^c$R$^c$, —[NHC(O)]$_n$R$^a$, —[NR$^a$C(O)]$_n$R$^a$, —[NHC(O)]$_n$OR$^a$, —[NR$^a$C(O)]$_n$OR$^a$, —[NHC(O)]$_n$NR$^c$R$^c$, —[NR$^a$C(O)]$_n$NR$^c$R$^c$, —[NHC(NH)]$_n$NR$^c$R$^c$ and —[NR$^a$C(NR$^a$)]$_n$NR$^c$R$^c$;

each $R^c$ is, independently of the others, selected from the group consisting of a protecting group and $R^a$, or, alternatively, the two $R^c$ bonded to the same nitrogen atom are taken together with that nitrogen atom to form a 5 to 8-membered cycloheteroalkyl or heteroaryl which may optionally include one or more of the same or different additional heteroatoms and which may optionally be substituted with one or more of the same or different $R^a$ groups;

$R^{21}$, $R^{22}$ and $R^{23}$ are each, independently of one another, selected from the group consisting of hydrogen and a progroup $R^P$;

$R^P$ has the formula —(CR$^d$R$^d$)$_y$-A-R$^3$, where y is an integer ranging from 1 to 3; A is O or S; each R$^d$ is, independently of the others, selected from the group consisting of hydrogen, optionally substituted lower alkyl, optionally substituted (C6-C14) aryl and optionally substituted (C7-C20) arylalkyl; where the optional substituents are, independently of one another, selected from hydroxyl, lower alkoxy, (C6-C14) aryloxy, lower alkoxyalkyl and halogen, or, alternatively, two R$^d$ bonded to the same carbon atom, taken together with the carbon atom to which they are bonded, form a cycloalkyl group containing from 3 to 8 carbon atoms;

R$^3$ comprises, together with the heteroatom, A, to which it is bonded, an alcohol, an ether, a thioether, a silyl ether, a silyl thioether, an ester, a thioester, an amide, a carbonate, a thiocarbonate, a carbamate, a thiocarbamate, a urea, a phosphate, a phosphate salt or a phosphate ester;

each m is, independently of the others, an integer from 1 to 3; and each n is, independently of the others, an integer from 0 to 3, with the proviso that at least one of $R^{21}$, $R^{22}$, and $R^{23}$ is $R^P$.

In therapeutic use, the compounds of the present invention are usually administered in a standard pharmaceutical composition. The present invention therefore provides, in a further aspect, a pharmaceutical composition comprising a compound of formula (I) and a pharmaceutically acceptable carrier.

In a particular embodiment, there is one progroup $R^P$, and in more particular embodiments, $R^{21}$ is $R^P$. In one exemplary embodiment the prodrug is a prodrug of Compound 1. In a specific example, the compound is N4-(2,2-dimethyl-4-[(dihydrogen phosphonoxy)methyl]-3-oxo-5-pyrido[1,4]oxazin-6-yl)-5-fluoro-N2-(3,4,5-trimethoxyphenyl)-2,4-pyrimidinediamine and salts thereof, Compound 4.

Compound 4

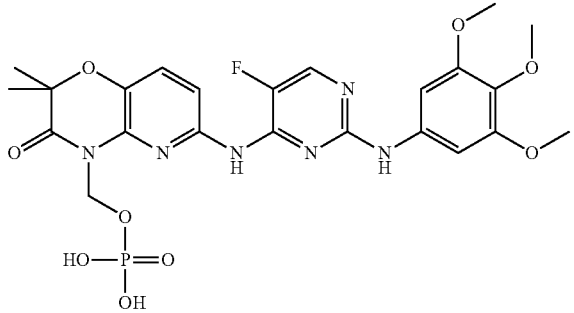

When used to treat or prevent such diseases, the active compounds may be administered singly, as mixtures of one or more active compounds or in mixture or combination with other agents useful for treating such diseases and/or the symptoms associated with such diseases. The active compounds may also be administered in mixture or in combination with agents useful to treat other disorders or maladies, such as anti-hypertensives (such as beta blockers, angiotensin-converting enzyme (ACE) inhibitors and calcium channel blockers), cholesterol medications (such as statin, fibrates, or intestinal cholesterol absorption-inhibiting supplements, including ezetimibe), anticoagulants (e.g., heparin or warfarin), anti-platelet medications (e.g., low-dose aspirin), niacin, omega-3 fatty acids, and folic acids. The active compounds may be administered per se in the form of prodrugs or as pharmaceutical compositions, comprising an active compound or prodrug.

Pharmaceutical compositions comprising the active compounds of the invention (or prodrugs thereof) may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the active compounds into preparations which can be used pharmaceutically.

The active compound or prodrug may be formulated in the pharmaceutical compositions per se, or in the form of a hydrate, solvate, N-oxide or pharmaceutically acceptable salt, as previously described. Typically, such salts are more soluble in aqueous solutions than the corresponding free acids and bases, but salts having lower solubility than the corresponding free acids and bases may also be formed.

Pharmaceutical compositions of the invention may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the active compound(s) or prodrug(s) may be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives.

Alternatively, the injectable formulation may be provided in powder form for reconstitution with a suitable vehicle, including but not limited to sterile pyrogen free water, buffer, dextrose solution, etc., before use. To this end, the active compound(s) maybe dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars, films or enteric coatings. Compounds which are particularly suitable for oral administration include 6-(5-fluoro-2-(3,4,5-trimethoxyphenylamino)pyrimidin-4-ylamino)-2,2-dimethyl-2H-pyrido[3,2-b][1,4]oxazin-3(4H)-one and prodrugs thereof, for example but not limited to, (6-(5-fluoro-2-(3,4,5-trimethoxyphenylamino)pyrimidin-4-ylamino)-2,2-dimethyl-3-oxo-2H-pyrido[3,2-b][1,4]oxazin-4(3H)-yl)methyl dihydrogen phosphate and pharmaceutically acceptable salts thereof.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, CREMOPHORE™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the active compound or prodrug, as is well known.

For buccal administration, the compositions may take the form of tablets or lozenges formulated in conventional manner.

For rectal and vaginal routes of administration, the active compound(s) may be formulated as solutions (for retention enemas) suppositories or ointments containing conventional suppository bases such as cocoa butter or other glycerides.

For nasal administration or administration by inhalation or insufflation, the active compound(s) or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

A specific example of an aqueous suspension formulation suitable for nasal administration using commercially-available nasal spray devices includes the following ingredients: active compound or prodrug (0.5-20 mg/ml); benzalkonium chloride (0.1-0.2 mg/mL); polysorbate 80 (TWEEN® 80; 0.5-5 mg/ml); carboxymethylcellulose sodium or microcrystalline cellulose (1-15 mg/ml); phenylethanol (1-4 mg/ml); and dextrose (20-50 mg/ml). The pH of the final suspension can be adjusted to range from about pH 5 to pH 7, with a pH of about pH 5.5 being typical.

Another specific example of an aqueous suspension suitable for administration of the compounds via inhalation, and in particular for such administration of a 2,4-pyrimidinediamine, contains 1-20 mg/mL Compound or prodrug, 0.1-1% (v/v) Polysorbate 80 (TWEEN® 80), 50 mM citrate and/or 0.9% sodium chloride.

For prolonged delivery, the active compound(s) or prodrug(s) can be formulated as a depot preparation for administration by implantation or intramuscular injection. The active ingredient maybe formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption may be used. To this end, permeation enhancers may be used to facilitate-transdermal penetration of the active compound(s). Suitable transdermal patches are: described in for example, U.S. Pat. No. 5,407,713; U.S. Pat. No. 5,352,456; U.S. Pat. No. 5,332,213; U.S. Pat. No. 5,336,168; U.S. Pat. No. 5,290,561; U.S. Pat. No. 5,254,346; U.S. Pat. No. 5,164,189; U.S. Pat. No. 5,163,899; U.S. Pat. No. 5,088,977; U.S. Pat. No. 5,087,240; U.S. Pat. No. 5,008,110; and U.S. Pat. No. 4,921,475.

Alternatively, other pharmaceutical delivery systems may be employed. Liposomes and emulsions are well-known examples of delivery vehicles that may be used to deliver active compound(s) or prodrug(s). Certain organic solvents such as dimethylsulfoxide (DMSO) may also be employed, although usually at the cost of greater toxicity.

The pharmaceutical compositions may, if desired, be presented in a pack or dispenser device which may contain one or more unit dosage forms containing the active compound(s). The pack may, for example, comprise metal or plastic foil, such as a blister pack. The pack or dispenser device may be accompanied by instructions for administration.

The active compound(s) or prodrug(s) of the invention, or compositions thereof, will generally be used in an amount effective to achieve the intended result, for example in an amount effective to treat or prevent the particular disease being treated. The compound(s) may be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. For example, administration of a compound to a patient suffering from atherosclerosis provides therapeutic benefit not only when the underlying deposition of lipids and resulting arterial blockage is eradicated or ameliorated, but also when the patient reports a decrease in the severity or duration of the cardiovascular symptoms. As another example, therapeutic benefit in the context of atherosclerosis includes decreased rates of lipid deposition, decreased atherogenesis, or a reduction in the frequency or severity of cardiac episodes. Therapeutic benefit also includes halting or slowing the progression of the disease, regardless of whether improvement is realized.

For prophylactic administration, the compound may be administered to a patient at risk of developing atherosclerosis. Alternatively, prophylactic administration may be applied to avoid the onset of symptoms in a patient diagnosed with the underlying disorder. Compounds may also be administered prophylactically to apparently healthy individuals who are genetically prone to developing atherosclerosis.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, etc. Determination of an effective dosage is well within the capabilities of those skilled in the art.

Effective dosages may be estimated initially from in vitro assays. For example, an initial dosage for use in animals may be formulated to achieve a circulating blood or serum concentration of active compound that is at or above an $IC_{50}$ of the particular compound as measured in as in vitro assay, such as the in vitro CHMC, platelet or other in vitro assays described in the Examples section. Calculating dosages to achieve such circulating blood or serum concentrations taking into account the bioavailability of the particular compound is well within the capabilities of skilled artisans. For guidance, the reader is referred to Fingl & Woodbury, "General Principles," In: Goodman and Gilman's The Pharmaceutical Basis of Therapeutics, Chapter 1, pp. 1-46, latest edition, Pagamonon Press, and the references cited therein.

Initial dosages can also be estimated from in vivo data, such as animal models. Animal models useful for testing the efficacy of compounds to treat or prevent the various diseases described above are well-known in the art. Suitable animal models of atherosclerosis are described in Zadelaar, et al., "Mouse models for atherosclerosis and pharmaceutical modifiers," Arterioscler. thromb. Vasc. Biol. 27(8):1706-21 (2007). Ordinarily skilled artisans can routinely adapt such information to determine dosages suitable for human administration. Additional suitable animal models are described in the Examples section.

Dosage amounts will typically be in the range of from about 0.0001 or 0.001 or 0.01 mg/kg/day to about 100 mg/kg/day, but may be higher or lower, depending upon, among other factors, the activity of the compound, its bioavailability, the mode of administration and various factors discussed above. Dosage amount and interval may be adjusted individually to provide plasma levels of the compound(s) which are sufficient to maintain therapeutic or prophylactic effect. For example, the compounds may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of active compound(s) may not be related to plasma concentration. Skilled artisans will be able to optimize effective local dosages without undue experimentation.

Preferably, the compound(s) will provide therapeutic or prophylactic benefit without causing substantial toxicity. Toxicity of the compound(s) may be determined using standard pharmaceutical procedures. The dose ratio between toxic and therapeutic (or prophylactic) effect is the therapeutic index. Compounds(s) that exhibit high therapeutic indices are preferred.

Compounds of the present invention may also be of use in treating the above mentioned disease states in combination with an anti-hyperlipidaemic, anti-atherosclerotic, anti-diabetic, anti-anginal, anti-inflammatory, or anti-hypertension agent or an agent for lowering Lp(a). Examples of the above include cholesterol synthesis inhibitors such as statins, antioxidants such as probucol, insulin sensitisers, calcium channel antagonists, and anti-inflammatory drugs such as NSAIDs. Examples of agents for lowering Lp(a) include the aminophosphonates described in WO 97/02037, WO 98/28310, WO 98/28311 and WO 98/28312 (Symphar SA and SmithKline Beecham).

A preferred combination therapy will be the use of a compound of the present invention and a statin. The statins are a well known class of cholesterol lowering agents and include atorvastatin, simvarstatin, pravastatin, cerivastatin, fluvastatin, lovastatin and rosuvastatin (also referred to as S-4522 or ZD 4522, Astra Zeneca). The two agents may be administered at substantially the same time or at different times, according to the discretion of the physician.

A further preferred combination therapy will be the use of a compound of the present invention and an anti-diabetic agent or an insulin sensitiser, as coronary heart disease is a major cause of death for diabetics. Within this class, preferred compounds for use with a compound of the present invention include the PPARgamma activators, for instance G1262570

(GlaxoSmithKline) and the glitazone class of compounds such as rosiglitazone (Avandia, GlaxoSmithKline), troglitazone and pioglitazone.

The 2,4-pyrimidinediamine compounds and prodrugs of the invention can be synthesized via a variety of different synthetic routes using commercially available starting materials and/or starting materials prepared by conventional synthetic methods. Suitable exemplary methods that can be routinely adapted to synthesize the 2,4-pyrimidinediamine compounds and prodrugs of the invention are found in U.S. Pat. No. 5,958,935, the disclosure of which is incorporated herein by reference. Specific examples describing the synthesis of numerous 2,4-pyrimidinediamine compounds and prodrugs, as well as intermediates therefore, are described in U.S. Pat. No. 7,060,827, the contents of which are incorporated herein by reference. Suitable exemplary methods that can be routinely used and/or adapted to synthesize active 2,4-pyrimidinediamine compounds can also be found in international application Serial No. PCT/US03/03022 filed Jan. 31, 2003 (WO 03/063794), U.S. application Ser. No. 10/631,029 filed Jul. 29, 2003, international application Serial No. PCT/US03/24087 (WO2004/014382), U.S. application Ser. No. 10/903,263 filed Jul. 30, 2004, and international application Serial No. PCT/US2004/24716 (WO005/016893), the disclosures of which are incorporated herein by reference. All of the compounds described herein (including prodrugs) can be prepared by routine adaptation of these methods.

Exemplary synthetic methods for the 2,4-substituted pyrimidinediamines are described in U.S. Pat. No. 7,060,827 and U.S. Patent Publication No. 2007-0203161 A1, incorporated herein by reference. Those of skill in the art will also be able to readily adapt these methods for the synthesis of specific 2,4-substituted pyrimidinediamines as described therein. Skilled artisans will recognize that in some instances certain substituents, such as, for example, $R^2$ and/or $R^4$, may include functional groups requiring protection. The exact identity of the protecting group used will depend upon, among other things, the identity of the functional group being protected and the reaction conditions used in the particular synthetic scheme, and will be apparent to those of skill in the art. Guidance for selecting protecting groups, their attachment and removal suitable for a particular application can be found, for example, in Greene & Wuts, supra.

Prodrugs as described herein can be prepared by routine modification of the above-described methods. Alternatively, such prodrugs can be prepared by reacting a suitably protected 2,4-pyrimidinediamine 6 with a suitable progroup. Conditions for carrying out such reactions and for deprotecting the product to yield a prodrugs as described herein are well-known.

Myriad references teaching methods useful for synthesizing pyrimidines generally, as well as starting materials described in Schemes (I)-(VII), are known in the art. For specific guidance, the reader is referred to Brown, D. J., "The Pyrimidines", in *The Chemistry of Heterocyclic Compounds, Volume* 16 (Weissberger, A., Ed.), 1962, Interscience Publishers, (A Division of John Wiley & Sons), New York ("Brown I"); Brown, D. J., "The Pyrimidines", in *The Chemistry of Heterocyclic Compounds, Volume 16, Supplement I* (Weissberger, A. and Taylor, E. C., Ed.), 1970, Wiley-Interscience, (A Division of John Wiley & Sons), New York (Brown II"); Brown, D. J., "The Pyrimidines", in *The Chemistry of Heterocyclic Compounds, Volume 16, Supplement II* (Weissberger, A. and Taylor, E. C., Ed.), 1985, An Interscience Publication (John Wiley & Sons), New York ("Brown III"); Brown, D. J., "The Pyrimidines" in *The Chemistry of Heterocyclic Compounds, Volume* 52 (Weissberger, A. and Taylor, E. C., Ed.), 1994, John Wiley & Sons, Inc., New York, pp. 1-1509 (Brown IV"); Kenner, G. W. and Todd, A., in *Heterocyclic Compounds*, Volume 6, (Elderfield, R. C., Ed.), 1957, John Wiley, New York, Chapter 7 (pyrimidines); Paquette, L. A., *Principles of Modern Heterocyclic Chemistry*, 1968, W. A. Benjamin, Inc., New York, pp. 1-401 (uracil synthesis pp. 313, 315; pyrimidinediamine synthesis pp. 313-316; amino pyrimidinediamine synthesis pp. 315); Joule, J. A., Mills, K. and Smith, G. F., *Heterocyclic Chemistry*, $3^{rd}$ Edition, 1995, Chapman and Hall, London, UK, pp. 1-516; Vorbrüggen, H. and Ruh-Pohlenz, C., *Handbook of Nucleoside Synthesis*, John Wiley & Sons, New York, 2001, pp. 1-631 (protection of pyrimidines by acylation pp. 90-91; silylation of pyrimidines pp. 91-93); Joule, J. A., Mills, K. and Smith, G. F., *Heterocyclic Chemistry*, $4^{th}$ Edition, 2000, Blackwell Science, Ltd, Oxford, UK, pp. 1-589; and *Comprehensive Organic Synthesis*, Volumes 1-9 (Trost, B. M. and Fleming, I., Ed.), 1991, Pergamon Press, Oxford, UK.

Those of skill in the art will appreciate that the 2,4-pyrimidinediamine compounds described herein may include functional groups that can be masked with progroups to create prodrugs. Such prodrugs are usually, but need not be, pharmacologically inactive until converted into their active drug form. Indeed, many of the 2,4-pyrimidinediamine compounds described in this invention include promoieties that are hydrolyzable or otherwise cleavable under conditions of use. For example, ester groups commonly undergo acid-catalyzed hydrolysis to yield the parent carboxylic acid when exposed to the acidic conditions of the stomach, or base-catalyzed hydrolysis when exposed to the basic conditions of the intestine or blood. Thus, when administered to a subject orally, 2,4-pyrimidinediamine compounds that include ester moieties can be considered prodrugs of their corresponding carboxylic acid, regardless of whether the ester form is pharmacologically active.

The mechanism by which the progroup(s) metabolizes is not critical, and can be caused by, for example, hydrolysis under the acidic conditions of the stomach, as described above, and/or by enzymes present in the digestive tract and/or tissues or organs of the body. Indeed, the progroup(s) can be selected to metabolize at a particular site within the body. For example, many esters are cleaved under the acidic conditions found in the stomach. Prodrugs designed to cleave chemically in the stomach to the active 2,4-pyrimidinediamine can employ progroups including such esters. Alternatively, the progroups can be designed to metabolize in the presence of enzymes such as esterases, amidases, lipolases, phosphatases including ATPases and kinase etc. Progroups including linkages capable of metabolizing in vivo are well-known, and include, by way of example and not limitation, ethers, thioethers, silylethers, silylthioethers, esters, thioesters, carbonates, thiocarbonates, carbamates, thiocarbamates, ureas, thioureas, carboxamides, etc. In some instances, a "precursor" group that is oxidized by oxidative enzymes such as, for example, cytochrome P450 of the liver, to a metabolizable group, can be selected.

In the prodrugs, any available functional moiety can be masked with a progroup to yield a prodrug. Functional groups within the 2,4-pyrimidinediamine compounds that can be masked with progroups for inclusion in a promoiety include, but are not limited to, amines (primary and secondary), hydroxyls, sulfanyls (thiols), carboxyls, etc. Myriad progroups suitable for masking such functional groups to yield promoieties that are cleavable under the desired conditions of use are known in the art. All of these progroups, alone or in combinations, can be included in the prodrugs.

In some embodiments of the 2,4-pyrimidinediamine compounds and methods of using the compounds, the progroup(s) can be attached to any available primary or secondary amine, including, for example, the N2 nitrogen atom of the 2,4-pyrimidinediamine moiety, the N4 nitrogen atom of the 2,4-pyrimidinediamine moiety, and/or a primary or secondary nitrogen atom included in a substituent on the 2,4-pyrimidinediamine compound.

In particular embodiments of the 2,4-pyrimidinediamine compounds and methods of using the compounds, the prodrugs described herein are 2,4-pyrimidinediamine compounds that are substituted at the N4 nitrogen of the 2,4-pyrimidinediamine moiety with a substituted or unsubstituted nitrogen-containing bicyclic ring that includes at least one progroup at one or more of: the nitrogen atom(s) of the bicyclic ring, the N2 nitrogen of the 2,4-pyrimidinediamine moiety and/or the N4 nitrogen of the 2,4-pyrimidinediamine moiety.

As noted above, the identity of the progroup is not critical, provided that it can be metabolized under the desired conditions of use, for example under the acidic conditions found in the stomach and/or by enzymes found in vivo, to yield a the biologically active group, e.g., the 2,4-substituted pyrimidinediamines as described herein. Thus, skilled artisans will appreciate that the progroup can comprise virtually any known or later-discovered hydroxyl, amine or thiol protecting group. Non-limiting examples of suitable protecting groups can be found, for example, in *Protective Groups in Organic Synthesis*, Greene & Wuts, 2nd Ed., John Wiley & Sons, New York, 1991 (especially pages 10-142 (alcohols, 277-308 (thiols) and 309-405 (amines) the disclosure of which is incorporated herein by reference).

Additionally, the identity of the progroup(s) can also be selected so as to impart the prodrug with desirable characteristics. For example, lipophilic groups can be used to decrease water solubility and hydrophilic groups can be used to increase water solubility. In this way, prodrugs specifically tailored for selected modes of administration can be obtained. The progroup can also be designed to impart the prodrug with other properties, such as, for example, improved passive intestinal absorption, improved transport-mediated intestinal absorption, protection against fast metabolism (slow-release prodrugs), tissue-selective delivery, passive enrichment in target tissues, targeting-specific transporters, etc. Groups capable of imparting prodrugs with these characteristics are well-known, and are described, for example, in Ettmayer et al., 2004, J. Med. Chem. 47(10):2393-2404, the disclosure of which is incorporated by reference. All of the various groups described in these references can be utilized in the prodrugs described herein.

In another embodiment, the present invention relates to a prosthetic device suitable for use or implantation into a subject, preferably a human. The device is coated with a composition containing a pyrimidinediamine of the invention. The device is preferably a stent. The formulated materials used in accordance with the present invention comprise a pyrimidinediamine having Syk inhibitory activity.

In such an embodiment, the compounds of the invention may be coated or sealed on a prosthetic device which is suitable, e.g., for implantation or other use in a subject, preferably a human. Examples of such devices include, but are not limited to, all types of angioplasty devices including a stent or stent/graft, or a commercial synthetic vascular graft or a biologic vascular graft. Any stent, stent/graft or tissue engineered vascular graft ("tubes") known in the art can be coated or sealed with the compounds of the present invention. The tubes can be metallic, or made from a biocompatible polymer, as well as a biodegradable polymer, such as, e.g., dacron polyester, poly(ethylene terephthalate), polycarbonate, polymethylmethacrylate, polypropylene, polyalkylene oxalates, polyvinylchloride, polyurethanes, polysiloxanes, nylons, poly(dimethyl siloxane), polycyanoacrylates, polyphosphazenes, poly(amino acids), ethylene glycol I dimethacrylate, poly(methyl methacrylate), poly(2-hydroxyethyl methacrylate), poly(HEMA), polyhydroxyalkanoates, polytetrafluorethylene, polycarbonate, poly(glycolide-lactide) co-polymer, polylactic acid, poly(.epsilon.-caprolactone), poly(.beta.-hydroxybutyrate), polydioxanone, poly(γ-ethyl glutamate), polyiminocarbonates, poly(ortho ester), polyanhydrides, alginate, dextran, chitin, cotton, polyglycolic acid, polyurethane, or derivatized versions thereof, i.e., polymers which have been modified to include, for example, attachment sites or cross-linking groups in which the polymers retain their structural integrity while allowing for attachment of molecules, such as proteins, nucleic acids, and the like. The tubes can also be fabric-coated metal structures. The tubes can also be made from combinations of metal and polymer. The tubes can be configured into any desired shape or conformation, such as, for example, linear, tapered, bifurcated, etc., and may be prepared using fiber technology, such as, e.g., crimped, woven, knitted, velour, double velour, with or without coils. The tubes can also be prepared by chemical extrusion, casting or molding using, for example, porous materials having linear or random pores that are circular or geometric in shape.

There are a variety of methods of manufacture available to provide a prosthetic device, coated on at least one surface with a sufficient amount of a compound of the present invention. The resulting coating is preferably uniform and should be integral so that contact between the device surface(s) and the surrounding tissue is precluded. The compounds can be applied to the device by spraying at least one surface of the device with the compounds in suspension, and allowing the applied surface to dry. In another embodiment, the device can be dipped into such a suspension, or by casting a suspension of the compounds over the device, or by layering a device the a suspension of the compounds over the device, or by impregnating a device with a suspension of the compounds. The compounds may be applied to the inside surface of a tube. By applying the compounds on the inside of the tube, the compounds promote proper reendothelialization of the lumen wall, promote wound healing and prevent or inhibit one or more cardiovascular disease states, such as stenosis, restenosis or intimal and neointimal hyperplasias.

The particular amount of the preparation to be applied to the device can be easily determined empirically by comparing devices with different amounts of the compound coated thereon and determining the efficacy of each by, for example, measuring. Also, one skilled in the relevant art and who is familiar with standard treatments would also be in a position to easily evaluate the efficacy of a device. Moreover, more than one coat of the compounds, either untreated or crosslinked, can be applied to a device. It is highly desirable to inspect the device once coated to insure that there are no gaps or breaks present in the coating.

Other methods of coating stents are well known in the art and are contemplated by the invention, for example, U.S. Pat. No. 5,637,113 describes coating stents with a polymer film, U.S. Pat. No. 5,837,313 describes a drug release stent coating process; both of these patents are incorporated herein in their entireties and for all purposes.

In a specific embodiment, a stent coated with the compounds the present invention, is provided. The compounds in or on the stent may be complexed with a drug, such as an antibiotic agent or an antiviral agent, or mixtures thereof, in order to insure against graft rejection. Additional drugs which may be added to the coating include antiplatelets, antithrombins, cytostatic and antiproliferative agents for example.

The methods used for implanting the coated devices are analogous to those used for the implantation of such devices without the coating, and, of course, depend on the nature of the condition to be modified or corrected. The surgery can be performed under either local or systemic anesthesia and, generally, involves an incision, spacing to accommodate the implant, insertion, and suture.

The invention having been described, the following examples are offered by way of illustration and not limitation.

V. EXAMPLES

A. Example 1

2,4-Pyrimidinediamines Inhibit αIgM-Induced CD69 Expression in Primary B-Cells

Human BJAB B cells were routinely cultured in RPMI 1640 medium supplemented with 10% FCS (JRH Biosciences, Lenexa, Kans.), penicillin, and streptomycin. The BJAB cells were split to $2.5 \times 10^5$ cells/ml 24-hours before stimulation. Cells were spun and resuspended at $5 \times 10^5$ cells/ml in fresh complete RPMI 1640 medium in the presence of 5 or 10 μg/ml anti-IgM F(ab')2 (Jackson ImmunoResearch, West Grove, Pa.), at 37° C., and then assayed for surface CD69 expression. CD69 is a marker expressed y B cells activated via the B cell receptor (BCR). These activated cells are the source of autoantibodies and of a wide variety of inflammatory cytokines believed to play a role in atherosclerosis (*Physiol. Rev.* 86: 515-581 (2006)).

TABLE 1

| EC50 (μM) | [αIgM] μg/mL | Stimulation Time (hrs) | Donor |
|---|---|---|---|
| 0.215 | 5 | 6 | A |
| 0.195 | 5 | 6 | B |
| 0.239 | 10 | 6 | C* | n = 2 per data point;
*primary B-cells were obtained from AllCells.

B. Example 2

2,4-Pyrimidinediamines Inhibit Mast Cell Activation Induced by FcγR Cross-Linking Human mast cells were cultured and differentiated from CD38-negative progenitor cell as described in U.S. Patent Publication No. 2005-234049, incorporated herein by reference. For example, 65 μl of various concentrations of 6-(5-fluoro-2-(3,4,5-trimethoxyphenylamino) pyrimidin-4-ylamino)-2,2-dimethyl-2H-pyrido[3,2-b][1,4]oxazin-3(4H)-one (compound 1), prepared in MT (137 mM NaCl, 2.7 mM KCl, 1.8 mM CaCl$_2$, 1.0 mM MgCl$_2$, 5.6 mM Glucose, 20 mM Hepes (pH 7.4), 0.1% Bovine Serum Albumin, (Sigma A4503)) containing 2% MeOH and 1% DMSO, or control buffer were added to duplicate 96-well V-bottom plates. Pelleted and resuspended (in warm MT) CHMC cells (65 μl) were added to each 96-well plate, mixed and incubated for 1 hr at 37° C. 25 μl of 6× anti-IgG Rabbit anti-human IgG, Affinity purified (Bethyl Laboratories Cat No. A80-105A3) final concentration 1 μg/ml, was added to the test wells. MT (25 μl) was added to control wells. After a 60-minute incubation at 37° C., cells and cell debris were pelleted by centrifugation at 1000 rpm for 10 min and tryptase and leukotriene C$_4$ levels were measured.

To measure tryptase levels, 25 μl of supernatant from each well was transferred to a fresh 96-well black bottom plate, to which 100 μl of fresh tryptase substrate solution [(Z-Ala-Lys-Arg-AMC2TFA; Enzyme Systems Products, #AMC-246)] 1:2000 in tryptase assay buffer [0.1 M Hepes (pH 7.5), 10% w/v Glycerol, 10 μM Heparin (Sigma H-4898) 0.01% NaN$_3$] was added. After 30 min incubation at room temperature, the optical density of the plates is measured at 355 nm/460 nm on a spectrophotometric plate reader. Table 2 provides the IC$_{50}$.

Leukotriene C4 (LTC4) levels were quantified using an ELISA kit on appropriately diluted supernatant samples following the supplier's instructions (Cayman Chemical Co., Cat No. 520211).

Inhibition of release and/or synthesis of lipid mediators was assessed by measuring the release of LTC4 and inhibition of release and/or synthesis of cytokines was monitored by quantifying TNFα, IL-8, GM-CSF, IL-10 and IL-13. Cytokine (TNFα, IL-8, GM-CSF, IL-10, IL-13) production was measured 6-8 hrs post-IgG crosslinking. Leukotriene and cytokine levels were quantified using the following commercial ELISA kits: LTC4 (Cayman Chemical #520211), TNFα (Biosource #KHC3011), GM-CSF (Biosource #KHC0901), IL-10 (Biosource #KHC0122), and IL-13 (Biosource #KHC0132).

TABLE 2

| | EC$_{50}$ (μM) | | | | | | |
|---|---|---|---|---|---|---|---|
| Compound | Degranulation (tryptase) | LTC4 | TNFα | IL-8 | GMCSF | IL-10 | IL-13 |
| lot A | 0.053 | 0.036 | 0.045 | 0.045 | 0.046 | 0.125 | 0.090 |
| lot B | 0.076 | 0.047 | 0.120 | 0.062 | 0.067 | 0.148 | 0.148 |

C. Example 4

2,4-Pyrimidinediamines Activate Platelets Via a Syk-Mediated Pathway

Human peripheral blood, from healthy volunteers who had not taken any medication for at least 7 days, was drawn into Vacutainer-ACD tubes (Acid citrate dextrose (ACD) Solution Tubes, VWR Cat. No. VT4606). Platelet-rich plasma (PRP) and platelet-poor plasma (PPP) were prepared by differential centrifugation (200 g and >2500 g, respectively, 20 min, RT). Platelets in PRP were incubated for 10 min at 37° C. with test article-DMSO solutions that had been previously diluted in MT buffer (137 mM NaCl, 2.7 mM KCl, 1.8 mM CaCl$_2$, 1.0 mM MgCl$_2$, 5.6 mM glucose, 20 mM Hepes, 0.1% BSA; pH 7.4). The test articles included dimethyl Sulfoxide (DMSO) (Sigma-Aldrich, Cat No. D2650), wortmannin *Penicillium funiculosum* (Sigma-Aldrich, Cat No. W1628), and 6-(5-fluoro-2-(3,4,5-trimethoxyphenylamino)pyrimidin-4-ylamino)-2,2-dimethyl-2H-pyrido[3,2-b][1,4]oxazin-3(4H)-one (compound 1).

Cells were stimulated with collagen (Chronolog Corp. Cat. No. 385) at 20 μg/mL, adenosine 5'-diphosphate (ADP) (Sigma-Aldrich Cat. No. A2754) at 33 μM, or phorbol 12-Myristate 13-Acetate (PMA) (Sigma-Aldrich Cat. No. P8139) at 33 ng/mL, for 15 min at 37° C., then incubated with staining antibody (anti-CD62P PE) at RT in the dark for 20 min, and fixed with paraformaldehyde (Cytofix fixation buffer) in the dark for 30 min at RT. Finally, cells were washed with PBS containing 2% fetal bovine serum and stored at 4° C. in the dark prior to flow cytometry. Measurements were performed using a FACScalibur flow cytometer (BD Biosciences, San Jose, Calif., USA). CD62P expression was expressed as geometric mean fluorescence on the vertical axis. See FIG. 2.

Compound 1 inhibited collagen receptor mediated platelet activation. However, compound 1 did not inhibit CD62P surface upregulation in platelets induced by ADP or PMA, confirming that compound 1 is acting upon platelets via a Syk-dependent pathway, i.e., collagen-mediated signaling.

We claim:

1. A method of treating atherosclerosis or regressing or decreasing formation of arterial atherosclerotic lesions, said method comprising administering to a mammal having atherosclerosis an effective amount of N4-(2,2-dimethyl-4-[(dihydrogen phosphonoxy)methyl]-3-oxo-5-pyrido[1,4]oxazin-6-yl)-5-fluoro-N2-(3,4,5-trimethoxyphenyl)-2,4-pyrimidinediamine or a salt thereof.

* * * * *